(12) United States Patent
Wagner-Hattler et al.

(10) Patent No.: US 11,737,984 B2
(45) Date of Patent: Aug. 29, 2023

(54) DOSAGE FORM

(71) Applicant: Omya International AG, Oftringen (CH)

(72) Inventors: Leonie Wagner-Hattler, Allschwil (CH); Maxim Puchkov, Pfeffingen (CH); Jörg Huwyler, Arlesheim (CH); Laura De Miguel, Oftringen (CH); Carolina Diaz Quijano, Oftringen (CH); Joachim Schoelkopf, Oberkulm (CH)

(73) Assignee: Omya International AG, Oftringen (CH)

( * ) Notice: Subject to any disclaimer, the term of this patent is extended or adjusted under 35 U.S.C. 154(b) by 0 days.

(21) Appl. No.: 16/304,991

(22) PCT Filed: Jul. 13, 2017

(86) PCT No.: PCT/EP2017/067704
§ 371 (c)(1),
(2) Date: Nov. 27, 2018

(87) PCT Pub. No.: WO2018/011343
PCT Pub. Date: Jan. 18, 2018

(65) Prior Publication Data
US 2020/0155458 A1    May 21, 2020

Related U.S. Application Data

(60) Provisional application No. 62/364,913, filed on Jul. 21, 2016.

(30) Foreign Application Priority Data

Jul. 14, 2016  (EP) ..................................... 16179526

(51) Int. Cl.
*A61K 9/20*    (2006.01)
*A23L 33/16*   (2016.01)
(Continued)

(52) U.S. Cl.
CPC ............ *A61K 9/2009* (2013.01); *A23L 33/16* (2016.08); *A23P 10/28* (2016.08); *A61K 9/2072* (2013.01);
(Continued)

(58) Field of Classification Search
None
See application file for complete search history.

(56) References Cited

U.S. PATENT DOCUMENTS

| 3,976,764 A | 8/1976 | Watanabe et al. |
| 4,451,260 A | 5/1984 | Mitra |

(Continued)

FOREIGN PATENT DOCUMENTS

| DE | 35 27 852 A1 | 2/1986 |
| EP | 0 338 861 A2 | 10/1989 |

(Continued)

OTHER PUBLICATIONS

Fukuda et al. "Floating hot-melt extruded tablets for gastroretentive controlled drug release system", Journal of Controlled Release 115 (2006) 121-129. (Year: 2006).*

(Continued)

*Primary Examiner* — Isis A Ghali
(74) *Attorney, Agent, or Firm* — Schwegman Lundberg & Woessner, P.A.

(57) ABSTRACT

The present invention relates to a dosage form comprising at least one functionalized calcium carbonate-comprising material (FCC) and at least one hot melt extruded polymer resin, a method for producing same, a pharmaceutical, (Continued)

nutraceutical, cosmetic, home and personal care product comprising the dosage form and the uses thereof.

4 Claims, 3 Drawing Sheets

(51) Int. Cl.
  *A23P 10/28* (2016.01)
  *A61K 31/155* (2006.01)
(52) U.S. Cl.
  CPC .......... *A61K 9/2095* (2013.01); *A61K 31/155* (2013.01); *A23V 2002/00* (2013.01)

(56) References Cited

U.S. PATENT DOCUMENTS

| | | | |
|---|---|---|---|
| 4,627,977 | A | 12/1986 | Gaffar et al. |
| 4,814,179 | A | 3/1989 | Bolton et al. |
| 4,985,459 | A | 1/1991 | Sunshine et al. |
| 2003/0099741 | A1 | 5/2003 | Gubler |
| 2003/0157213 | A1 | 8/2003 | Jenkins |
| 2003/0206993 | A1 | 11/2003 | Gubler |
| 2004/0020410 | A1 | 2/2004 | Gane et al. |
| 2009/0088465 | A1 | 4/2009 | Dyar et al. |
| 2010/0010050 | A1 | 1/2010 | Reizlein et al. |
| 2012/0077878 | A1* | 3/2012 | Berner ................ A61P 1/00 514/578 |

FOREIGN PATENT DOCUMENTS

| | | | |
|---|---|---|---|
| EP | 0 717 988 | A1 | 6/1996 |
| EP | 2 264 108 | A1 | 12/2010 |
| EP | 2 264 109 | A1 | 12/2010 |
| EP | 2 272 536 | A2 | 1/2011 |
| EP | 2 719 373 | A1 | 4/2014 |
| EP | 2 719 376 | A1 | 4/2014 |
| EP | 2 770 017 | A1 | 8/2014 |
| EP | 2 975 078 | A1 | 1/2016 |
| EP | 3 034 070 | A1 | 6/2016 |
| FR | 2787802 | B1 | 2/2001 |
| JP | 2008521878 | | 6/2008 |
| JP | 2010501497 | | 1/2010 |
| WO | 00/39222 | A1 | 7/2000 |
| WO | 2004/083316 | A1 | 9/2004 |
| WO | 2005/121257 | A2 | 12/2005 |
| WO | 2006059224 | | 6/2006 |
| WO | 2008022745 | | 2/2008 |
| WO | 2009/074492 | A1 | 6/2009 |
| WO | 2010/146530 | A1 | 12/2010 |
| WO | 2010/146531 | A1 | 12/2010 |
| WO | 2014/001063 | A1 | 1/2014 |
| WO | WO-2015071394 | A1 * | 5/2015 ............ A23K 40/25 |
| WO | WO-2015097031 | A1 | 7/2015 |

OTHER PUBLICATIONS

Merriam Webster Dictionary, Definition of "loaded with" (Year: 2022).*
Morott et al. "The effect of screw configuration and polymeric carrier on hot-melt extruded taste-masked formulations incorporated into orally disintegrating tablets", Journal of Pharmaceutical Sciences 104:124-134 (Year: 2015).*
International Search Report dated Sep. 29, 2017 from PCT/EP2017/067704.
Written Opinion of the International Searching Authority dated Sep. 29, 2017 from PCT/EP2017/067704.
"Japanese Application Serial No. 2019-501568, Notice of Reasons for Refusal dated Aug. 3, 2021", w/ English Translation, 10 pgs.
Pertsev, Im, et al., "CH 11: Excipients and Their Use in Pharmacy", Pharmaceutical and biomedical aspects of drugs: vol. 1—Khar'kov: UcrPha, w/ English Machine Translation, (1999), 8 pgs.
Preisig, Daniel, et al., "Drug loading into porous calcium carbonate microparticles by solvent evaporation", European Journal of Pharmaceutics and Biopharmaceutics, vol. 87, (2014), 548-558.

* cited by examiner

DOSAGE FORM

CROSS-REFERENCE TO RELATED APPLICATIONS

This is a U.S. national phase of PCT Application No. PCT/EP2017/067704, filed Jul. 13, 2017, which claims priority to U.S. Provisional Application No. 62/364,913, filed Jul. 21, 2016 and European Application No. 16179526.5, filed Jul. 14, 2016.

The present invention relates to a dosage form comprising at least one functionalized calcium carbonate-comprising material (FCC) and at least one hot melt extruded polymer resin, a method for producing same, a pharmaceutical, nutraceutical, cosmetic, home and personal care product comprising the dosage form and the uses thereof.

In many products such as pharmaceutical, nutraceutical, cosmetic, home and personal care products dosage forms such as tablets, mini-tablets, granules, pellets or capsules are used for providing active and/or inactive agents. Such dosage forms are mainly manufactured out of powders. Depending on the final use, the carrier material or matrix for such dosage forms is typically mixed with the required active and/or inactive agent and further compatible disintegrants need to be found in order to be able to produce a dosage form. A frequent problem arising for such dosage form is, that they typically do not allow for a high ratio of active and/or inactive agents to carrier material or matrices and thus resulting in dosage forms being relatively heavy and voluminous at low loading of active and/or inactive agents.

Numerous carriers have been used in such dosage forms including waxes, oils, fats, soluble polymers, and the like. Another approach provides to disperse the active and/or inactive agent throughout a solid matrix material through which said active and/or inactive agent is released by diffusion. Still another approach provides to enclose the dosage form within a capsule having polymeric walls through which said active and/or inactive agent can pass by diffusion.

For example, Pawar et al. (Gastroretentive dosage forms: A review with special emphasis on floating drug delivery systems. Drug Delivery. 2011 February; 18(2):97-110) considered floating drug delivery systems (FDDS) as an easy and logical approach regarding formulation and technical aspects for the development of GRDDS.

U.S. Pat. No. 3,976,764 discloses an instantly floating tablet, having a hollow sphere based on gelatin coated with several under-coatings, wherein a therapeutically active ingredient is comprised in one of the under-coatings.

DE 35 27 852 A1 discloses a pharmaceutical formulation with a specific density below 1, wherein a substance forming a gel in water is mixed with a pharmaceutically active agent and a fat/oil which is solid at room temperature. The gel forming substance being a derivative of cellulose, dextran or starch.

EP 0 338 861 A2, refers to an antacid composition with prolonged gastric residence time. The antacid such as Hydrotalcite or Amalgate forming a solid core which is surrounded by a solid external phase containing a hydrophobic substance e.g. an ester of glycerol with palmitic or stearic acid, hydroxylated polyalkene and a non-ionic emulsifier.

EP 0 717 988 A1, refers to a swollen moulding which is an expanded structure having a mesh-like cross-section and an apparent density of less than 1, which structure is predominantly an acid-resistant polymer compound and additionally containing at least an auxiliary blowing agent and a drug substance. Because of its mesh-like structure in cross-section, the swollen moulding of the invention has a multiplicity of microfine internal pores which are continuous or discontinuous. Said acid-resistant polymer compound are chosen, e.g. from hydroxypropymethylcellulose acetate succinate or phthalate.

U.S. Pat. No. 4,451,260 refers to a multilayered structure comprising a pharmaceutical active ingredient wherein air is entrapped in the multilayered structure, thus promoting flotation.

U.S. Pat. No. 4,814,179 refers to a floating sustained release therapeutic composition. Non-compressed sustained release tablets comprise a hydrocolloid gelling agent, a therapeutically acceptable inert oil, the selected therapeutic agent and water.

EP 2 719 376 A1 refers to gastroretentive drug formulations and delivery systems using functionalized calcium carbonate and their method of preparation.

In this regard, calcium carbonate seems to be promising for the preparation of pharmaceutical delivery system as it exhibits a highly porous meshwork with lamellar surface structure that grips particles strongly together, see e.g. EP 2 719 373 A1. It thus offers the possibility to formulate them in to granules, pellets, capsules or to compact them into tablets or mini-tablets.

A new type of surface-reacted calcium carbonate was first described in FR 2787802 B1 in the year of 1998, subsequently in WO 00/39222 A1 and US 2004/0020410 A1, and is based on the reaction of natural ground calcium carbonate with gaseous $CO_2$ and with one or more medium-strong to strong $H_3O^+$ ion providers. The obtained product is a porous calcium carbonate having a special surface structure, porosity, and specific surface area providing a reduction in the weight of paper for a constant surface area without loss of physical properties, when it is used as a pigment or coating filler for the said paper.

In WO 2004/083316 A1, a further advantageous modification in the preparation of this surface-reacted calcium carbonate is described, wherein aluminium silicate, synthetic silica, calcium silicate, silicates and/or monovalent salt are involved, and which are also useful in paper-making applications. Also, WO 2005/121257 A2 refers to the addition of advantageous additives in the production of said surface-reacted calcium carbonate, wherein one or more compounds of formula R—X are added, which, e.g. are selected from fatty acids, fatty amines or fatty alcohols. WO 2009/074492 A1 especially relates to the optimization of the known process as regards precipitated calcium carbonate, as it turned out that due to the special conditions in the precipitation of calcium carbonate, the process useful for natural ground calcium carbonate did not provide the same good results for the surface-reaction of synthetic precipitated calcium carbonate. Several further optimizations and modifications of the process for the preparation of surface-reacted calcium carbonate followed such as those described in EP 2 264 108 A1 (WO 2010/146530 A1) and EP 2 264 109 A1 (WO 2010/146531 A1) involving the use of weak acids in the preparation of surface-reacted calcium carbonate.

In WO2014/001063 relates to a high solids aqueous mineral filler suspension which maintains its mechanical properties of a suspension at low temperatures and acidic environment.

The European Patent application EP 3 034 070 A1 of the present applicant refers to roller compacting of a mixture comprising a functionalized natural- or synthetic calcium carbonate, an active pharmaceutical ingredient and/or inactive precursor, and one or more formulating aids and compacting the roller compacted mixture thus obtained into a pharmaceutical delivery system. The unpublished European patent application EP 16 175 590.5 refers to method for producing a dosage form, comprising the steps of: a) providing a surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source; b) providing at least one active ingredient and/or inactive precursor thereof; c) loading the surface-reacted calcium carbonate of step a) with the at least one active ingredient and/or inactive precursor thereof of step b); d) compacting the loaded surface-reacted calcium carbonate obtained in step c) by means of a roller compacter at a compaction pressure in the range from 1 to 30 kN/cm into a compacted form; and e) milling the compacted form of step d) into granules; with the proviso that the compacted form of the loaded surface-reacted calcium carbonate obtained in step d) consists of the surface-reacted calcium carbonate of step a) and the at least one active ingredient and/or inactive precursor thereof of step b). The unpublished European Patent application 16 175 595.4 refers to a method for the production of granules comprising surface-reacted calcium carbonate, comprising the steps of: a) providing a surface-reacted calcium carbonate, wherein the surface-reacted calcium carbonate is a reaction product of natural ground or precipitated calcium carbonate with carbon dioxide and one or more $H_3O^+$ ion donors in an aqueous medium, wherein the carbon dioxide is formed in-situ by the $H_3O^+$ ion donor treatment and/or is supplied from an external source; b) compacting the surface-reacted calcium carbonate of step a) by means of a roller compacter at a compaction pressure in the range from 1 to 30 kN/cm into a compacted form; c) milling the compacted form of step b) into granules; wherein the compacted form obtained in step b) consists of the surface-reacted calcium carbonate of step a).

The unpublished European Patent application 15 160 194.5 of the present applicant refers to a method for producing a dispersible dosage form in an aqueous environment comprises the steps of: a) providing a functionalized natural and/or synthetic calcium carbonate-comprising material, which is a reaction product of natural ground or precipitated calcium carbonate with carbon dioxide and one or more acids in an aqueous medium, wherein the carbon dioxide is formed in situ by the acid treatment and/or is supplied from an external source, b) providing at least one disintegrant; c) optionally providing at least one further formulating aid; d) mixing the at least one functionalized natural and/or synthetic calcium carbonate-comprising material of step a), the at least one disintegrant of step b) and the optionally at least one further formulating aid of step c); and e) compacting the mixture obtained in step d) by means of a roller compactor at a compaction pressure in the range from 2 to 20 bar into a ribbon; and f) milling the ribbon of step e) into granules and g) sieving of the granules of step f) by at least one mesh size.

Throughout the present invention and in view of the cited prior art, surface reacted (natural or synthetic) calcium carbonate is equivalent to functionalized (natural and/or synthetic) calcium carbonate-comprising material.

However, there is a continuous need for dosage forms which provide a better performance than existing dosage forms and especially for dosage forms being lighter and less voluminous at higher active and/or inactive agent load, preferably compared to a conventional dosage form comprising a functionalized calcium carbonate-comprising material. There is also a continuous need for methods for the production of a dosage form and especially allows for producing a dosage form being lighter and less voluminous at higher active and/or inactive agent load, preferably compared to a conventional dosage form comprising a functionalized calcium carbonate-comprising material. Furthermore, it is desired to provide methods for producing dosage forms which are efficient and allows for the direct compression of the dosage form without the use of binders and/or compacting aids.

It is thus an object of the present invention to provide a dosage form. Another object may also be seen in the provision of a dosage form being lighter and less voluminous at higher active and/or inactive agent load, especially compared to a conventional dosage form comprising a functionalized calcium carbonate-comprising material. A further object may be seen in the provision of a method for producing a dosage form. Another object may also be seen in the provision of a method for producing a dosage form being lighter and less voluminous at higher active and/or inactive agent load, especially compared to a conventional dosage form comprising a functionalized calcium carbonate-comprising material. A still further object may also be seen in the provision of a highly efficient compression method of the dosage form without the use of binders and/or compacting aids.

One or more of the foregoing and other problems are solved by the subject-matter as defined herein in the independent claims. Advantageous embodiments of the present invention are defined in the corresponding sub-claims.

A first aspect of the present invention relates to a dosage form comprising
   a) at least one functionalized calcium carbonate-comprising material (FCC), which is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source,
   b) at least one hot melt extruded polymer resin,
   wherein the at least one functionalized calcium carbonate-comprising material is dispersed in the at least one hot melt extruded polymer resin and the weight ratio of functionalized calcium carbonate-comprising material to hot melt extruded polymer resin (FCC/polymer) ranges from 95:5 to 5:95.

According to another aspect of the present invention, the use of the dosage form as defined herein, in a pharmaceutical, nutraceutical, cosmetic, home and personal care product is provided. According to a further aspect of the present invention, a pharmaceutical, nutraceutical, cosmetic, home and personal care product comprising the dosage form, as defined herein, is provided.

According to a further aspect of the present invention, a method for producing a dosage form is provided. The method comprising the steps of:
   a) providing at least one functionalized calcium carbonate-comprising material (FCC), which is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, as defined herein;
   b) providing at least one polymer resin as defined herein;

c) mixing the at least one functionalized calcium carbonate-comprising material of step a) and the at least one polymer resin of step b);
d) hot melt extruding the mixture obtained in step c); and
e) milling or pelletizing the hot melt extruded product obtained in step d) for obtaining the dosage form.

According to one embodiment of the present method, the method further comprises a step b1) of providing at least one active agent and/or inactive agent, preferably the at least one active agent and/or inactive agent is selected from the group comprising pharmaceutical active agents, active or inactive prodrugs, nutraceuticals, food additives, cosmetic additives and mixtures thereof, and/or a step b2) of providing at least one excipient, preferably the at least one excipient is selected from the group comprising a disintegrant, especially selected form the group comprising modified cellulose gums, insoluble cross-linked polyvinylpyrrolidones, starch glycolates, micro crystalline cellulose, pregelatinized starch, sodium carboxymethyl starch, low-substituted hydroxypropyl cellulose, homopolymers of N-vinyl-2-pyrrolidone, alkyl-, hydroxyalkyl-, carboxyalkyl-cellulose esters, alginates, microcrystalline cellulose and its polymorphic forms, ion exchange resins, gums, chitin, chitosan, clays, gellan gum, crosslinked polacrillin copolymers, agar, gelatine, dextrines, acrylic acid polymers, carboxymethylcellulose sodium/calcium, hydroxypropyl methyl cellulose phthalate, shellac or mixtures thereof, lubricants, inner-phase lubricants, outer-phase lubricants, impact modifiers, plasticizers, waxes, stabilizers, pigments, coloring agents, scenting agents, taste masking agents, flavoring agents, sweeteners, mouth-feel improvers, binders, diluents, film forming agents, adhesives, buffers, adsorbents, odour-masking agents and mixtures thereof.

According to another embodiment of the present method, the at least one active agent and/or inactive agent of step b1) and/or the at least one excipient of step b2) is/are
a) loaded onto or mixed with the at least one functionalized calcium carbonate-comprising material (FCC) prior to mixing step c), and/or
b) mixed with the at least one functionalized calcium carbonate-comprising material of step a) and the at least one polymer resin of step b) in mixing step c) prior to hot melt extruding step d), and/or
c) coated in form of one or more layers onto the dosage form obtained in step e).

According to yet another embodiment of the present method, the method comprises one or more steps f) of compacting the dosage form obtained in step e).

According to one embodiment of the present method, the at least one active agent and/or inactive agent of step b1) and/or the at least one excipient of step b2) is/are mixed and compacted in compacting step f1) to form a core tablet.

According to another embodiment of the present method, further comprising a step g) of at least partially covering the core tablet formed in step f1) with the dosage form obtained in step e) and compacting the obtained product.

According to yet another embodiment of the present method, the same or different at least one active agent and/or inactive agent of step b1) and/or at least one excipient of step b2) is/are
a) loaded onto the at least one functionalized calcium carbonate-comprising material (FCC) prior to mixing step c), and/or
b) mixed with the at least one functionalized calcium carbonate-comprising material of step a) and the at least one polymer resin of step b) in mixing step c) prior to hot melt extruding step d).

According to an even further aspect of the present invention, the use of functionalized calcium carbonate-comprising material (FCC), as defined herein, in a method for producing a dosage form is provided. According to a still further aspect of the present invention, the use of functionalized calcium carbonate-comprising material (FCC), as defined herein, in a dosage form such as a tablet, mini-tablet, pellet, capsule, granule and/or a tablet-in-cup is provided.

According to one embodiment of the present dosage form, the natural ground calcium carbonate is selected from calcium carbonate containing minerals selected from the group comprising marble, chalk, dolomite, limestone and mixtures thereof; or the precipitated calcium carbonate is selected from the group comprising precipitated calcium carbonates having aragonitic, vateritic or calcitic mineralogical crystal forms and mixtures thereof.

According to another embodiment of the present dosage form, the at least one functionalized calcium carbonate-comprising material
a) has a BET specific surface area of from 20 $m^2/g$ to 450 $m^2/g$, preferably from 20 $m^2/g$ to 250 $m^2/g$, more preferably from 30 $m^2/g$ to 160 $m^2/g$, most preferably from 40 $m^2/g$ to 150 $m^2/g$, still more preferably from 50 $m^2/g$ to 140 $m^2/g$ measured using the nitrogen and BET method according to ISO 9277; and/or
b) comprises particles having a volume median grain diameter $d_{50}$ (vol) of from 1 μm to 50 μm, preferably from 1 to 45 μm, more preferably from 2 to 30 μm, even more preferably from 3 to 15 μm, and most preferably from 4 to 12 μm; and/or
c) has an intra-particle intruded specific pore volume within the range of 0.15 to 1.35 $cm^3/g$, preferably of 0.30 to 1.30 $cm^3/g$, more preferably of 0.40 to 1.25 $cm^3/g$, calculated from a mercury intrusion porosimetry measurement.

According to yet another embodiment of the present dosage form, the at least one hot melt extruded polymer resin is selected from the group comprising polyethylene, polystyrene, polyvinylchloride, polyamide 66 (nylon), polycaprolactame, polycaprolactone, acrylic polymers, acrylonitrile butadiene styrene, polybenzimidazole, polycarbonate, polyphenylene oxide/sulfide, polypopylene, teflon, polylactic acid, polylactic acid-based polymer, aliphatic polyester such as polyhydroxybutyrate, poly-3-hydroxybutyrate (P3HB), polyhydroxyvalerate, polyhydroxybutyrate-polyhydroxyvalerate copolymer, poly(3-hydroxybutyrate-co-3-hydroxyvalerate), polyglyconate, poly(dioxanone) and mixtures thereof, preferably the at least one polymer resin is selected from polycaprolactone, polylactic acid, polylactic acid-based polymer and mixtures thereof.

According to one embodiment of the present dosage form, the dosage form further comprises at least one active agent and/or inactive agent.

According to another embodiment of the present dosage form, the at least one active agent and/or inactive agent is selected from the group comprising pharmaceutical active agents, active or inactive prodrugs, nutraceuticals, food additives, cosmetic additives and mixtures thereof.

According to yet another embodiment of the present dosage form, the at least one active agent and/or inactive agent is/are
a) loaded onto or mixed with the at least one functionalized calcium carbonate-comprising material (FCC), and/or
b) dispersed in the at least one hot melt extruded polymer resin comprising the at least one functionalized calcium carbonate-comprising material (FCC), and/or c) is in form of a core, preferably in form of a compacted tablet, which is at least partially covered by the at least one hot melt extruded polymer resin comprising the at least one functionalized calcium carbonate-comprising material (FCC), or d) in form of a layer which at least partially covers a core, preferably a compacted tablet, made from the at least one hot melt extruded polymer resin comprising the at least one functionalized calcium carbonate-comprising material (FCC), or e) in form of a layered structure of at least two layers, wherein at least one layer is made from the hot melt extruded polymer resin comprising the at least one functionalized calcium carbonate-comprising material (FCC).

According to one embodiment of the present dosage form, the dosage form further comprises at least one excipient, preferably the at least one excipient is selected from the group comprising a disintegrant, especially selected form the group comprising modified cellulose gums, insoluble cross-linked polyvinylpyrrolidones, starch glycolates, micro crystalline cellulose, pregelatinized starch, sodium carboxymethyl starch, low-substituted hydroxypropyl cellulose, homopolymers of N-vinyl-2-pyrrolidone, alkyl-, hydroxyalkyl-, carboxyalkyl-cellulose esters, alginates, microcrystalline cellulose and its polymorphic forms, ion exchange resins, gums, chitin, chitosan, clays, gellan gum, crosslinked polacrillin copolymers, agar, gelatine, dextrines, acrylic acid polymers, carboxymethylcellulose sodium/calcium, hydroxpropyl methyl cellulose phthalate, shellac or mixtures thereof, lubricants, inner-phase lubricants, outer-phase lubricants, impact modifiers, plasticizers, waxes, stabilizers, pigments, coloring agents, scenting agents, taste masking agents, flavoring agents, sweeteners, mouth-feel improvers, binders, diluents, film forming agents, adhesives, buffers, adsorbents, odour-masking agents and mixtures thereof.

According to another embodiment of the present dosage form, the dosage form is in form of powder, tablets such as multi-layered tablets, tablets of altered geometric configuration or matrix-tablets, mini-tablets, pellets, capsules, granules and/or a tablet-in-cup.

It should be understood that for the purpose of the present invention the following terms have the following meaning.

For the purpose of the present invention, an "acid" is defined as Brønsted-Lowry acid, that is to say, it is an $H_3O^+$ ion provider. An "acid salt" is defined as an $H_3O^+$ ion-provider, e.g., a hydrogen-containing salt, which is partially neutralised by an electropositive element. A "salt" is defined as an electrically neutral ionic compound formed from anions and cations. A "partially crystalline salt" is defined as a salt that, on XRD analysis, presents an essentially discrete diffraction pattern.

In accordance with the present invention, $pK_a$ is the symbol representing the acid dissociation constant associated with a given ionisable hydrogen in a given acid, and is indicative of the natural degree of dissociation of this hydrogen from this acid at equilibrium in water at a given temperature. Such $pK_a$ values may be found in reference textbooks such as Harris, D. C. "Quantitative Chemical Analysis: $3^{rd}$ Edition", 1991, W.H. Freeman & Co. (USA), ISBN 0-7167-2170-8.

"Functionalized calcium carbonate-comprising material" is a material comprising calcium carbonate and a water insoluble, at least partially crystalline, non-carbonate calcium salt, preferably, extending from the surface of at least part of the calcium carbonate. The calcium ions forming said at least partially crystalline non-carbonate calcium salt originate largely from the starting calcium carbonate material that also serves to form the at least one functionalized natural and/or synthetic calcium carbonate-comprising material core. Such salts may include OH— anions and/or crystal water.

In the meaning of the present invention "water-insoluble" materials are defined as materials which, when mixed with deionised water and filtered on a filter having a 0.2 µm pore size at 20° C. to recover the liquid filtrate, provide less than or equal to 0.1 g of recovered solid material following evaporation at 95 to 100° C. of 100 g of said liquid filtrate. "Water-soluble" materials are defined as materials leading to the recovery of greater than 0.1 g of recovered solid material following evaporation at 95 to 100° C. of 100 g of said liquid filtrate.

"Natural ground calcium carbonate" (GCC) in the meaning of the present invention is a calcium carbonate obtained from natural sources, such as limestone, marble, dolomite, or chalk, and processed through a wet and/or dry treatment such as grinding, screening and/or fractionating, for example, by a cyclone or classifier. Said natural ground calcium carbonate being the base material for the functionalised natural calcium carbonate.

"Precipitated calcium carbonate" (PCC) in the meaning of the present invention is a synthesised material, obtained by precipitation following reaction of carbon dioxide and lime in an aqueous, semi-dry or humid environment or by precipitation of a calcium and carbonate ion source in water. PCC may be in the vateritic, calcitic or aragonitic crystal form. Said precipitated calcium carbonate being the base for the functionalised synthetic calcium carbonate.

Throughout the present document, the "particle size" of a calcium carbonate and other materials is described by its distribution of particle sizes. The value dx represents the diameter relative to which x % by weight of the particles have diameters less than $d_x$. This means that the $d_{20}$ value is the particle size at which 20 wt.-% of all particles are smaller, and the $d_{75}$ value is the particle size at which 75 wt.-% of all particles are smaller. The $d_{50}$ value is thus the weight median particle size, i.e. 50 wt.-% of all grains are bigger and the remaining 50 wt.-% of grains smaller than this particle size. For the purpose of the present invention the particle size is specified as weight median particle size $d_{50}$ unless indicated otherwise. For determining the weight median particle size $d_{50}$ value a Sedigraph can be used. For the purpose of the present invention, the "particle size" of functionalized calcium carbonate-comprising material is described as volume determined particle size distributions. For determining the volume determined particle size distribution, e.g., the volume median grain diameter ($d_{50}$) or the volume determined top cut particle size ($d_{98}$) of functionalized calcium carbonate-comprising material, a Malvern Mastersizer 2000 can be used. The weight determined particle size distribution may correspond to the volume determined particle size if the density of all the particles is equal.

A "specific surface area (SSA)" of a calcium carbonate in the meaning of the present invention is defined as the surface area of the calcium carbonate divided by its mass. As used herein, the specific surface area is measured by nitrogen gas adsorption using the BET isotherm (ISO 9277:2010) and is specified in $m^2/g$.

In the context of the present invention, the term "pore" is to be understood as describing the space that is found between and/or within particles, i.e. that is formed by the particles as they pack together under nearest neighbour contact (interparticle pores), such as in a powder or a compact and/or the void space within porous particles (intraparticle pores), and that allows the passage of liquids under pressure when saturated by the liquid and/or supports absorption of surface wetting liquids.

The "intraparticle intruded specific pore volume" according to the present invention can be calculated from a mercury intrusion porosimetry measurement and describes the measured pore volume that is found inside the pigment particles per unit mass of sample containing the particles. The intruded total specific void volume represents the sum of all the individual pore volumes, which can be intruded by mercury, per unit mass of the sample can be measured by mercury porosimetry using a Micrometrics Autopore IV mercury porosimeter. An exemplary mercury porosimetry experiment entails the evacuation of a porous sample to remove trapped gases, after which the sample is surrounded with mercury. The amount of mercury displaced by the sample allows calculation of the sample's bulk volume, $V_{bulk}$. Pressure is then applied to the mercury so that it intrudes into the sample through pores connected to the external surface. The maximum applied pressure of mercury can be 414 MPa, equivalent to a Laplace throat diameter of 0.004 μm. The data can be corrected using Pore-Comp (P. A. C. Gane et al. "Void Space Structure of Compressible Polymer Spheres and Consolidated Calcium Carbonate Paper-Coating Formulations", Industrial and Engineering Chemistry Research 1996, 35 (5):1753-1764) for mercury and penetrometer effects, and also for sample compression. By taking the first derivative of the cumulative intrusion curves the pore size distributions based on equivalent Laplace diameter, inevitably including the effect of pore-shielding when present, are revealed. The intruded total specific void volume corresponds to the void volume per unit mass of the sample determined by mercury porosimetry.

The term "polymer resin" in the meaning of the present invention refers to a polymeric material, either solid or liquid, preferably solid, prior to processing it into the hot melt extruded polymer resin.

The term "hot melt extruded" polymer resin refers to a polymer resin that has been processed by a hot melt extrusion process.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group, which preferably consists only of these embodiments.

Where an indefinite or definite article is used when referring to a singular noun, e.g. "a", "an" or "the", this includes a plural of that noun unless something else is specifically stated.

Terms like "obtainable" or "definable" and "obtained" or "defined" are used interchangeably. This e.g. means that, unless the context clearly dictates otherwise, the term "obtained" does not mean to indicate that e.g. an embodiment must be obtained by e.g. the sequence of steps following the term "obtained" though such a limited understanding is always included by the terms "obtained" or "defined" as a preferred embodiment.

According to the present invention it has been found that a dosage form comprising functionalized calcium carbonate-comprising material which is dispersed in at least one hot melt extruded polymer resin and wherein the weight ratio of functionalized calcium carbonate-comprising material to hot melt extruded polymer resin (FCC/polymer) ranges from 95:5 to 5:95, is lighter and less voluminous at higher drug load, especially compared to a conventional dosage form comprising a functionalized calcium carbonate-comprising material without using the at least one hot melt extruded polymer resin.

In the following, it is referred to further details of the present invention and especially the foregoing dosage form.

It is one requirement of the instant invention that the dosage form comprises at least one functionalized calcium carbonate-comprising material, which is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source. That is to say, the dosage form comprises at least one functionalized natural and/or synthetic calcium carbonate-comprising material, which is a reaction product of natural ground or precipitated calcium carbonate with carbon dioxide and one or more $H_3O^+$ ion donors, wherein the carbon dioxide is formed in situ by the $H_3O^+$ ion donors treatment and/or is supplied from an external source.

The expression "at least one" functionalized (natural and/or synthetic) calcium carbonate-comprising material means that one or more kinds of functionalized (natural and/or synthetic) calcium carbonate-comprising material may be present in the inventive dosage form.

Accordingly, the at least one functionalized (natural and/or synthetic) calcium carbonate-comprising material may be one kind of a functionalized (natural or synthetic) calcium carbonate-comprising material. Alternatively, the at least one functionalized (natural and/or synthetic) calcium carbonate-comprising material may be a mixture of two or more kinds of functionalized (natural and/or synthetic) calcium carbonate-comprising materials. For example, the at least one functionalized (natural and/or synthetic) calcium carbonate-comprising material may be a mixture of two or three kinds of functionalized (natural and/or synthetic) calcium carbonate-comprising materials. Preferably, the at least one functionalized (natural and/or synthetic) calcium carbonate-comprising material is one kind of a functionalized (natural or synthetic) calcium carbonate-comprising material.

Thus, the at least one functionalized calcium carbonate-comprising material, i.e. the at least one functionalized natural and/or synthetic calcium carbonate-comprising material, according to the present invention is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source.

A $H_3O^+$ ion donor in the context of the present invention is a Brønsted acid and/or an acid salt.

In a preferred embodiment of the invention the at least one functionalized calcium carbonate-comprising material, i.e. the at least one functionalized natural and/or synthetic calcium carbonate-comprising material, is obtained by a process comprising the steps of: (a) providing a suspension of natural or precipitated calcium carbonate, (b) adding at least one acid having a $pK_a$ value of 0 or less at 20° C. or having a $pK_a$ value from 0 to 2.5 at 20° C. to the suspension of step (a), and (c) treating the suspension of step (a) with carbon dioxide before, during or after step (b). According to another embodiment the at least one functionalized calcium carbonate-comprising material, i.e. the at least one functionalized natural and/or synthetic calcium carbonate-comprising material, is obtained by a process comprising the steps of: (A) providing a natural or precipitated calcium carbonate, (B) providing at least one water-soluble acid, (C) providing gaseous $CO_2$, (D) contacting said natural or precipitated calcium carbonate of step (A) with the at least one acid of step (B) and with the $CO_2$ of step (C), characterised in that: (i) the at least one acid of step B) has a $pK_a$ of greater than 2.5 and less than or equal to 7 at 20° C., associated with the ionisation of its first available hydrogen, and a corresponding anion is formed on loss of this first available hydrogen capable of forming a water-soluble calcium salt, and (ii) following contacting the at least one acid with natural or precipitated calcium carbonate, at least one water-soluble salt, which in the case of a hydrogen-containing salt has a $pK_a$ of greater than 7 at 20° C., associated with the ionisation of the first available hydrogen, and the salt anion of which is capable of forming water-insoluble calcium salts, is additionally provided.

"Natural ground calcium carbonate" (GCC) preferably is selected from calcium carbonate containing minerals selected from the group comprising marble, chalk, limestone and mixtures thereof. Natural calcium carbonate may comprise further naturally occurring components such as magnesium carbonate, alumino silicate etc.

In general, the grinding of natural ground calcium carbonate may be a dry or wet grinding step and may be carried out with any conventional grinding device, for example, under conditions such that comminution predominantly results from impacts with a secondary body, i.e. in one or more of: a ball mill, a rod mill, a vibrating mill, a roll crusher, a centrifugal impact mill, a vertical bead mill, an attrition mill, a pin mill, a hammer mill, a pulveriser, a shredder, a de-clumper, a knife cutter, or other such equipment known to the skilled man. In case the calcium carbonate containing mineral material comprises a wet ground calcium carbonate containing mineral material, the grinding step may be performed under conditions such that autogenous grinding takes place and/or by horizontal ball milling, and/or other such processes known to the skilled man. The wet processed ground calcium carbonate containing mineral material thus obtained may be washed and dewatered by well-known processes, e.g. by flocculation, filtration or forced evaporation prior to drying. The subsequent step of drying (if necessary) may be carried out in a single step such as spray drying, or in at least two steps. It is also common that such a mineral material undergoes a beneficiation step (such as a flotation, bleaching or magnetic separation step) to remove impurities.

"Precipitated calcium carbonate" (PCC) in the meaning of the present invention is a synthesized material, generally obtained by precipitation following reaction of carbon dioxide and calcium hydroxide in an aqueous environment or by precipitation of calcium and carbonate ions, for example $CaCl_2$ and $Na_2CO_3$, out of solution. Further possible ways of producing PCC are the lime soda process, or the Solvay process in which PCC is a by-product of ammonia production. Precipitated calcium carbonate exists in three primary crystalline forms: calcite, aragonite and vaterite, and there are many different polymorphs (crystal habits) for each of these crystalline forms. Calcite has a trigonal structure with typical crystal habits such as scalenohedral (S-PCC), rhombohedral (R-PCC), hexagonal prismatic, pinacoidal, colloidal (C-PCC), cubic, and prismatic (P-PCC). Aragonite is an orthorhombic structure with typical crystal habits of twinned hexagonal prismatic crystals, as well as a diverse assortment of thin elongated prismatic, curved bladed, steep pyramidal, chisel shaped crystals, branching tree, and coral or worm-like form. Vaterite belongs to the hexagonal crystal system. The obtained PCC slurry can be mechanically dewatered and dried.

According to one embodiment of the present invention, the precipitated calcium carbonate is precipitated calcium carbonate, preferably comprising aragonitic, vateritic or calcitic mineralogical crystal forms or mixtures thereof.

Precipitated calcium carbonate may be ground prior to the treatment with carbon dioxide and at least one $H_3O^+$ ion donor by the same means as used for grinding natural calcium carbonate as described above.

According to one embodiment of the present invention, the natural or precipitated calcium carbonate is in form of particles having a weight median particle size $d_{50}$ of 0.05 to 10.0 µm, preferably 0.2 to 5.0 µm, more preferably 0.4 to 3.0 µm, most preferably 0.6 to 1.2 µm, especially 0.7 µm. According to a further embodiment of the present invention, the natural or precipitated calcium carbonate is in form of particles having a top cut particle size $d_{98}$ of 0.15 to 55 µm, preferably 1 to 40 µm, more preferably 2 to 25 µm, most preferably 3 to 15 µm, especially 4 µm.

The natural and/or precipitated calcium carbonate may be used dry or suspended in water. Preferably, a corresponding slurry has a content of natural or precipitated calcium carbonate within the range of 1 wt.-% to 90 wt.-%, more preferably 3 wt.-% to 60 wt.-%, even more preferably 5 wt.-% to 40 wt.-%, and most preferably 10 wt.-% to 25 wt.-% based on the weight of the slurry.

The one or more $H_3O^+$ ion donor used for the preparation of the at least one functionalized calcium carbonate-comprising material, i.e. the at least one functionalized natural and/or synthetic calcium carbonate-comprising material, may be any strong acid, medium-strong acid, or weak acid, or mixtures thereof, generating $H_3O^+$ ions under the preparation conditions. According to the present invention, the at least one $H_3O^+$ ion donor can also be an acidic salt, generating $H_3O^+$ ions under the preparation conditions.

According to one embodiment, the at least one $H_3O^+$ ion donor is a strong acid having a $pK_a$ of 0 or less at 20° C.

According to another embodiment, the at least one $H_3O^+$ ion donor is a medium-strong acid having a $pK_a$ value from 0 to 2.5 at 20° C. If the $pK_a$ at 20° C. is 0 or less, the acid is preferably selected from sulphuric acid, hydrochloric acid, or mixtures thereof. If the $pK_a$ at 20° C. is from 0 to 2.5, the $H_3O^+$ ion donor is preferably selected from $H_2SO_3$, $H_3PO_4$, oxalic acid, or mixtures thereof. The at least one $H_3O^+$ ion donor can also be an acidic salt, for example, $HSO_4^-$ or $H_2PO_4^-$, being at least partially neutralized by a corresponding cation such as $Li^+$, $Na^+$ or $K^+$, or $HPO_4^{2-}$, being at least partially neutralised by a corresponding cation such as $Li^+$, $Na^+$, $K^+$, $Mg^{2+}$ or $Ca^{2+}$. The at least one $H_3O^+$ ion donor can also be a mixture of one or more acids and one or more acidic salts.

According to still another embodiment, the at least one $H_3O^+$ ion donor is a weak acid having a $pK_a$ value of greater than 2.5 and less than or equal to 7, when measured at 20° C., associated with the ionisation of the first available hydrogen, and having a corresponding anion, which is capable of forming water-soluble calcium salts. Subsequently, at least one water-soluble salt, which in the case of a hydrogen-containing salt has a $pK_a$ of greater than 7, when measured at 20° C., associated with the ionisation of the first available hydrogen, and the salt anion of which is capable of forming water-insoluble calcium salts, is additionally provided. According to the preferred embodiment, the weak acid has a $pK_a$ value from greater than 2.5 to 5 at 20° C., and more preferably the weak acid is selected from the group consisting of acetic acid, formic acid, propanoic acid, and mixtures thereof. Exemplary cations of said water-soluble salt are selected from the group consisting of potassium, sodium, lithium and mixtures thereof. In a more preferred embodiment, said cation is sodium or potassium. Exemplary anions of said water-soluble salt are selected from the group consisting of phosphate, dihydrogen phosphate, monohydrogen phosphate, oxalate, silicate, mixtures thereof and hydrates thereof. In a more preferred embodiment, said anion is selected from the group consisting of phosphate, dihydrogen phosphate, monohydrogen phosphate, mixtures thereof and hydrates thereof. In a most preferred embodiment, said anion is selected from the group consisting of dihydrogen phosphate, monohydrogen phosphate, mixtures thereof and hydrates thereof. Water-soluble salt addition may be performed dropwise or in one step. In the case of drop wise addition, this addition preferably takes place within a time period of 10 minutes. It is more preferred to add said salt in one step.

According to one embodiment of the present invention, the at least one $H_3O^+$ ion donor is selected from the group consisting of hydrochloric acid, sulphuric acid, sulphurous acid, phosphoric acid, citric acid, oxalic acid, acetic acid, formic acid, and mixtures thereof. Preferably the at least one $H_3O^+$ ion donor is selected from the group consisting of hydrochloric acid, sulphuric acid, sulphurous acid, phosphoric acid, oxalic acid, $H_2PO_4^-$, being at least partially neutralised by a corresponding cation such as $Li^+$, $Na^+$ or $K^+$, $HPO_4^{2-}$, being at least partially neutralised by a corresponding cation such as $Li^+$, $Na^+$, $K^+$, $Mg^{2+}$, or $Ca^{2+}$ and mixtures thereof, more preferably the at least one acid is selected from the group consisting of hydrochloric acid, sulphuric acid, sulphurous acid, phosphoric acid, oxalic acid, or mixtures thereof, and most preferably, the at least one $H_3O^+$ ion donor is phosphoric acid.

The one or more $H_3O^+$ ion donor can be added to the suspension as a concentrated solution or a more diluted solution. Preferably, the molar ratio of the $H_3O^+$ ion donor to the natural or precipitated calcium carbonate is from 0.01 to 4, more preferably from 0.02 to 2, even more preferably 0.05 to 1 and most preferably 0.1 to 0.58.

As an alternative, it is also possible to add the $H_3O^+$ ion donor to the water before the natural or precipitated calcium carbonate is suspended.

In a next step, the natural or precipitated calcium carbonate is treated with carbon dioxide. If a strong acid such as sulphuric acid or hydrochloric acid is used for the $H_3O^+$ ion donor treatment of the natural or precipitated calcium carbonate, the carbon dioxide is automatically formed. Alternatively or additionally, the carbon dioxide can be supplied from an external source.

$H_3O^+$ ion donor treatment and treatment with carbon dioxide can be carried out simultaneously which is the case when a strong or medium-strong acid is used. It is also possible to carry out $H_3O^+$ ion donor treatment first, e.g. with a medium strong acid having a $pK_a$ in the range of 0 to 2.5 at 20° C., wherein carbon dioxide is formed in situ, and thus, the carbon dioxide treatment will automatically be carried out simultaneously with the $H_3O^+$ ion donor treatment, followed by the additional treatment with carbon dioxide supplied from an external source.

Preferably, the concentration of gaseous carbon dioxide in the suspension is, in terms of volume, such that the ratio (volume of suspension):(volume of gaseous $CO_2$) is from 1:0.05 to 1:20, even more preferably 1:0.05 to 1:5.

In a preferred embodiment, the $H_3O^+$ ion donor treatment step and/or the carbon dioxide treatment step are repeated at least once, more preferably several times. According to one embodiment, the at least one $H_3O^+$ ion donor is added over a time period of at least about 5 min, preferably at least about 10 min, typically from about 10 to about 20 min, more preferably about 30 min, even more preferably about 45 min, and sometimes about 1 h or more.

Subsequent to the $H_3O^+$ ion donor treatment and carbon dioxide treatment, the pH of the aqueous suspension, measured at 20° C., naturally reaches a value of greater than 6.0, preferably greater than 6.5, more preferably greater than 7.0, even more preferably greater than 7.5, thereby preparing the at least one functionalized calcium carbonate-comprising material, i.e. the at least one functionalized natural and/or synthetic calcium carbonate-comprising material, as an aqueous suspension having a pH of greater than 6.0, preferably greater than 6.5, more preferably greater than 7.0, even more preferably greater than 7.5.

Further details about the preparation of the at least one functionalized natural calcium carbonate-comprising material are disclosed in WO 00/39222 A1, WO 2004/083316 A1, WO 2005/121257 A2, WO 2009/074492 A1, EP 2 264 108 A1, EP 2 264 109 A1 and US 2004/0020410 A1, the content of these references herewith being included in the present application.

Similarly, functionalized synthetic calcium carbonate-comprising material is obtained. As can be taken in detail from WO 2009/074492 A1, functionalized synthetic calcium carbonate is obtained by contacting precipitated calcium carbonate with $H_3O^+$ ions and with anions being solubilized in an aqueous medium and being capable of forming water-insoluble calcium salts, in an aqueous medium to form a slurry of functionalized synthetic calcium carbonate, wherein said functionalized synthetic calcium carbonate comprises an insoluble, at least partially crystalline calcium salt of said anion formed on the surface of at least part of the precipitated calcium carbonate.

Said solubilized calcium ions correspond to an excess of solubilized calcium ions relative to the solubilized calcium ions naturally generated on dissolution of precipitated calcium carbonate by $H_3O^+$ ions, where said $H_3O^+$ ions are provided solely in the form of a counterion to the anion, i.e. via the addition of the anion in the form of an acid or non-calcium acid salt, and in absence of any further calcium ion or calcium ion generating source.

Said excess solubilized calcium ions are preferably provided by the addition of a soluble neutral or acid calcium salt, or by the addition of an acid or a neutral or acid non-calcium salt which generates a soluble neutral or acid calcium salt in situ.

Said $H_3O^+$ ions may be provided by the addition of an acid or an acid salt of said anion, or the addition of an acid or an acid salt which simultaneously serves to provide all or part of said excess solubilized calcium ions.

In a further preferred embodiment of the preparation of the at least one functionalized calcium carbonate-comprising material, i.e. the at least one functionalized natural and/or synthetic calcium carbonate-comprising material, the natural or precipitated calcium carbonate is reacted with the one or more $H_3O^+$ ion donors and/or the carbon dioxide in the presence of at least one compound selected from the group consisting of silicate, silica, aluminium hydroxide, earth alkali aluminate such as sodium or potassium aluminate, magnesium oxide, or mixtures thereof. Preferably, the at least one silicate is selected from an aluminium silicate, a calcium silicate, or an earth alkali metal silicate. These components can be added to an aqueous suspension comprising the natural or precipitated calcium carbonate before adding the one or more $H_3O^+$ ion donors and/or carbon dioxide.

Alternatively, the silicate and/or silica and/or aluminium hydroxide and/or earth alkali aluminate and/or magnesium oxide component(s) can be added to the aqueous suspension of natural or precipitated calcium carbonate while the reaction of natural or precipitated calcium carbonate with the one or more $H_3O^+$ ion donors and carbon dioxide has already started. Further details about the preparation of the at least one functionalized calcium carbonate-comprising material, i.e. the at least one functionalized natural and/or synthetic calcium carbonate-comprising material, in the presence of at least one silicate and/or silica and/or aluminium hydroxide and/or earth alkali aluminate component (s) are disclosed in WO 2004/083316 A1, the content of this reference herewith being included in the present application.

The at least one functionalized calcium carbonate-comprising material, i.e. the at least one functionalized natural and/or synthetic calcium carbonate-comprising material, can be kept in suspension, optionally further stabilised by a dispersant. Conventional dispersants known to the skilled person can be used. A preferred dispersant is comprised of polyacrylic acids and/or carboxymethylcelluloses.

Alternatively, the aqueous suspension described above can be dried, thereby obtaining the solid (i.e. dry or containing as little water that it is not in a fluid form) at least one functionalized calcium carbonate-comprising material, i.e. the at least one functionalized natural and/or synthetic calcium carbonate-comprising material, in the form of granules or a powder.

The at least one functionalized calcium carbonate-comprising material, i.e. the at least one functionalized natural and/or synthetic calcium carbonate-comprising material, may have different particle shapes, such as e.g. the shape of roses, golf balls and/or brains.

Furthermore, in a preferred embodiment, the at least one functionalized calcium carbonate-comprising material, i.e. the at least one functionalized natural and/or synthetic calcium carbonate-comprising material, has a BET specific surface area of from 20.0 $m^2/g$ to 450.0 $m^2/g$, preferably from 20.0 $m^2/g$ to 250.0 $m^2/g$, more preferably from 30.0 $m^2/g$ to 160.0 $m^2/g$, even more preferably from 40.0 $m^2/g$ to 150.0 $m^2/g$, and most preferably from 50.0 $m^2/g$ to 140.0 $m^2/g$, measured using nitrogen and the BET method according to ISO 9277 77. The BET specific surface area in the meaning of the present invention is defined as the surface area of the particles divided by the mass of the particles. As used therein the specific surface area is measured by adsorption using the BET isotherm (ISO 9277:2010) and is specified in $m^2/g$.

According to one embodiment, the at least one functionalized calcium carbonate-comprising material, i.e. the at least one functionalized natural and/or synthetic calcium carbonate-comprising material, comprises particles having a volume median grain diameter $d_{50}$ (vol) of from 1 to 50 μm, preferably from 1 to 45 μm, more preferably from 2 to 30 μm, even more preferably from 3 to 15 μm, and most preferably from 4 to 12 μm.

Additionally or alternatively, the at least one functionalized calcium carbonate-comprising material, i.e. the at least one functionalized natural and/or synthetic calcium carbonate-comprising material, comprises particles having a grain diameter $d_{98}$ (vol) of less than or equal to 40.0 μm. preferably less than or equal to 30.0 μm, more preferably less than or equal to 25.0 μm, still more preferably of less than or equal to 20.0 μm, more preferably of less than or equal to 19.0 μm. Preferably, the at least one functionalized calcium carbonate-comprising material, i.e. the at least one functionalized natural and/or synthetic calcium carbonate-comprising material, comprises particles having a grain diameter $d_{98}$ (vol) in the range of from 5.0 to 40 μm, preferably form 6 to 30 μm, more preferably form 7.0 to 25.0 μm, still more preferably of from 10.0 to 20.0 μm, more preferably of from 11.0 to 19.0 μm.

The value $d_x$ represents the diameter relative to which x % of the particles have diameters less than $d_x$. This means that the $d_{98}$ value is the particle size at which 98% of all particles are smaller. The $d_{98}$ value is also designated as "top cut". The $d_x$ values may be given in volume or weight percent. The $d_{50}$ (wt) value is thus the weight median particle size, i.e. 50 wt.-% of all grains are smaller than this particle size, and the $d_{50}$ (vol) value is the volume median particle size, i.e. 50 vol.-% of all grains are smaller than this particle size.

Volume median grain diameter $d_{50}$ was evaluated using a Malvern Mastersizer 2000 Laser Diffraction System. The $d_{50}$ or $d_{98}$ value, measured using a Malvern Mastersizer 2000 Laser Diffraction System, indicates a diameter value such that 50% or 98% by volume, respectively, of the particles have a diameter of less than this value. The raw data obtained by the measurement are analysed using the Mie theory, with a particle refractive index of 1.57 and an absorption index of 0.005.

The weight median grain diameter is determined by the sedimentation method, which is an analysis of sedimentation behaviour in a gravimetric field. The measurement is made with a Sedigraph™ 5100 or 5120, Micromeritics Instrument Corporation. The method and the instrument are known to the skilled person and are commonly used to determine grain size of fillers and pigments. The measurement is carried out in an aqueous solution of 0.1 wt.-% $Na_4P_2O_7$. The samples were dispersed using a high speed stirrer and sonicated.

The processes and instruments are known to the skilled person and are commonly used to determine grain size of fillers and pigments.

The specific pore volume is measured using a mercury intrusion porosimetry measurement using a Micromeritics Autopore V 9620 mercury porosimeter having a maximum applied pressure of mercury 414 MPa (60 000 psi), equivalent to a Laplace throat diameter of 0.004 μm (~nm). The equilibration time used at each pressure step is 20 seconds. The sample material is sealed in a 5 $cm^3$ chamber powder penetrometer for analysis. The data are corrected for mercury compression, penetrometer expansion and sample material compression using the software Pore-Comp (Gane, P. A. C., Kettle, J. P., Matthews, G. P. and Ridgway, C. J., "Void Space Structure of Compressible Polymer Spheres and Consolidated Calcium Carbonate Paper-Coating Formulations", Industrial and Engineering Chemistry Research, 35(5), 1996, p 1753-1764).

The total pore volume seen in the cumulative intrusion data can be separated into two regions with the intrusion data from 214 μm down to about 1-4 μm showing the coarse packing of the sample between any agglomerate structures contributing strongly. Below these diameters lies the fine interparticle packing of the particles themselves. If they also have intraparticle pores, then this region appears bi modal, and by taking the specific pore volume intruded by mercury into pores finer than the modal turning point, i.e. finer than the bi-modal point of inflection, the specific intraparticle pore volume is defined. The sum of these three regions gives the total overall pore volume of the powder, but depends strongly on the original sample compaction/settling of the powder at the coarse pore end of the distribution.

By taking the first derivative of the cumulative intrusion curve the pore size distributions based on equivalent Laplace diameter, inevitably including pore-shielding, are revealed. The differential curves clearly show the coarse agglomerate pore structure region, the interparticle pore region and the intraparticle pore region, if present. Knowing the intraparticle pore diameter range it is possible to subtract the remainder interparticle and interagglomerate pore volume from the total pore volume to deliver the desired pore volume of the internal pores alone in terms of the pore volume per unit mass (specific pore volume). The same principle of subtraction, of course, applies for isolating any of the other pore size regions of interest.

Preferably, the at least one functionalized calcium carbonate-comprising material, i.e. the at least one functionalized natural and/or synthetic calcium carbonate-comprising material, has an intra-particle intruded specific pore volume within the range of 0.15 to 1.35 $cm^3/g$, preferably of 0.30 to 1.30 $cm^3/g$, and most preferably of 0.40 to 1.25 $cm^3/g$, calculated from mercury intrusion porosimetry measurement.

The pore diameter of the at least one functionalized calcium carbonate-comprising material, i.e. the at least one functionalized natural and/or synthetic calcium carbonate-comprising material, preferably is in a range of from 4 to 500 nm, more preferably in a range of between 20 and 80 nm, especially from 30 to 70 nm, e.g. 50 nm determined by mercury porosimetry measurement.

The intra-particle pore size of the surface-reacted calcium carbonate preferably is in a range of from 0.004 to 1.6 µm, more preferably in a range of from 0.005 to 1.3 µm, especially preferably from 0.006 to 1.15 µm and most preferably of 0.007 to 1.0 µm, determined by mercury porosimetry measurement.

According to a preferred embodiment the intra- and/or inter particle pores of the at least one functionalized calcium carbonate-comprising material, i.e. the at least one functionalized natural and/or synthetic calcium carbonate-comprising material, are hollow and, therefore, the at least one functionalized calcium carbonate-comprising material, i.e. the at least one functionalized natural and/or synthetic calcium carbonate-comprising material, is unloaded. In other words, the at least one functionalized calcium carbonate-comprising material, i.e. the at least one functionalized natural and/or synthetic calcium carbonate-comprising material, is not used as a carrying agent.

The at least one functionalized calcium carbonate-comprising material, i.e. the at least one functionalized natural and/or synthetic calcium carbonate-comprising material, may be in the form of dust or powder and preferably in the form of powder.

It is a further requirement of the present invention that the dosage form comprises at least one hot melt extruded polymer resin.

The expression "at least one" hot melt extruded polymer resin means that one or more kinds of hot melt extruded polymer resin may be present in the inventive dosage form.

Accordingly, the at least one hot melt extruded polymer resin may be one kind of a hot melt extruded polymer resin. Alternatively, the at least one hot melt extruded polymer resin may be a mixture of two or more kinds of hot melt extruded polymer resins. For example, the at least one hot melt extruded polymer resin may be a mixture of two or three kinds of hot melt extruded polymer resins. Preferably, the at least one hot melt extruded polymer resin is one kind of a hot melt extruded polymer resin.

It is appreciated that the at least one hot melt extruded polymer resin according to the present invention is not restricted to a specific resin material as long as the polymer resin is hot melt extruded, i.e. the unprocessed polymer resin must be suitable to be processed by hot melt extrusion. Furthermore, it is preferred that the at least one hot melt extruded polymer resin is suitable for the desired end use, e.g. is approved for human and/or animal consumption. For example, the at least one hot melt extruded polymer resin is a resin approved for medical use.

In one embodiment, the at least one hot melt extruded polymer resin is selected from the group comprising polyethylene, polystyrene, polyvinylchloride, polyamide 66 (nylon), polycaprolactame, polycaprolactone, acrylic polymers, acrylonitrile butadiene styrene, polybenzimidazole, polycarbonate, polyphenylene oxide/sulfide, polypopylene, teflon, polylactic acid, polylactic acid-based polymer, aliphatic polyester such as polyhydroxybutyrate, poly-3-hydroxybutyrate (P3HB), polyhydroxyvalerate, polyhydroxybutyrate-polyhydroxyvalerate copolymer, poly(3-hydroxybutyrate-co-3-hydroxyvalerate), polyglyconate, poly(dioxanone) and mixtures thereof.

In one embodiment the dosage form can be intended for consumption by animals or humans. Thus, the hot melt extruded polymer resin may be advantageously selected from a polymer resin that is known to be intended for such use.

In one embodiment, the at least one hot melt extruded polymer resin is thus preferably a hot melt extruded biodegradable and/or biocompatible polymer resin.

The term "biodegradable" polymer resin refers to a polymer resin that is capable of being broken down with the help of body fluids, bacteria or other living organisms, e.g. of the gastrointestinal tract, without producing harmful or toxic decomposition products.

The term "biocompatible" polymer resin within the meaning of the present application refers to a polymer resin that does not cause or provoke reactions within the human or animal body, e.g. no toxic or allergic response(s) to the biocompatible polymer resin is observed.

In one embodiment, the at least one hot melt extruded polymer resin is a hot melt extruded biodegradable and biocompatible polymer resin. Alternatively, the at least one hot melt extruded polymer resin is a hot melt extruded biodegradable or biocompatible polymer resin If the at least one hot melt extruded polymer resin is a hot melt extruded biodegradable and/or biocompatible polymer resin, the hot melt extruded polymer resin is preferably selected from the group comprising polycaprolactone, polylactic acid, polylactic acid-based polymer, aliphatic polyester such as polyhydroxybutyrate, poly-3-hydroxybutyrate (P3HB), polyhydroxyvalerate, polyhydroxybutyrate-polyhydroxyvalerate copolymer, poly(3-hydroxybutyrate-co-3-hydroxyvalerate), polyglyconate, poly(dioxanone) and mixtures thereof.

Preferably, the at least one hot melt extruded polymer resin, more preferably the at least one hot melt extruded biodegradable and/or biocompatible polymer resin, is selected from the group comprising polycaprolactone, polylactic acid, polylactic acid-based polymer and mixtures thereof.

For example, the at least one hot melt extruded polymer resin, preferably the at least one hot melt extruded biodegradable and/or biocompatible polymer resin, is polycaprolactone.

The at least one hot melt extruded polymer resin may be prepared in a well known manner and is/are commercially available from different manufacturers. For example, the medical grade polycaprolactone is available as Capa™ 6506 from Perstorp, Sweden.

In one embodiment of the present invention, the at least one hot melt extruded polymer resin has a melting temperature $T_m$ of above 40° C., more preferably in the range of from 40 to 200° C. and most preferably from 40 to 170° C.

Furthermore, it is appreciated that the at least one hot melt extruded polymer resin may be selected from polymer resins having a broad spectrum of melt flow rate. In general, it is preferred that the at least one hot melt extruded polymer resin has a melt flow rate MFR (160° C., 2.16 kg) measured according to ISO 1133 of from 1.0 to 120.0 g/10 min, preferably of from 2.0 to 100.0 g/10 min. For example, the at least one hot melt extruded polymer resin has a melt flow rate MFR (160° C., 2.16 kg) measured according to ISO 1133 of from 2.1 to 40.0 g/10 min or from 2.3 to 35.0 g/10 min.

For example, the at least one hot melt extruded biodegradable and/or biocompatible polymer resin, preferably polycaprolactone, has a melt flow rate MFR (160° C., 2.16 kg) measured according to ISO 1133 of from 2.0 to 100.0 g/10 min, preferably of from 2.3 to 35.0 g/10 min and most preferably from 2.3 to 15.0 g/10 min.

There is no specific limitation on the molecular weight of the at least one hot melt extruded polymer resin used in this invention. However, the weight average molecular weight of the at least one hot melt extruded polymer resin is preferably in the range of 20 000 to 5 000 000 g/mol, preferably in the range of 20 000 to 1 000 000 g/mol and most preferably in the range of 20 000 to 500 000 g/mol, e.g. in the range of 20 000 to 400 000 g/mol or in the range of 30 000 to 250 000 g/mol. If the weight average molecular weight is smaller than the aforementioned range, the mechanical strength (tensile strength, impact strength) of the polymer composition is too low. Polymer resin having a weight average molecular weight of up to 5 000 000 g/mol are described e.g. in EP 2 272 536, which disclosure is thus herewith incorporated by reference.

The weight average molecular weight of the at least one hot melt extruded biodegradable and/or biocompatible polymer resin, preferably polycaprolactone, is preferably in the range of 20 000 to 400 000 g/mol, preferably in the range of 30 000 to 300 000 g/mol and most preferably in the range of 30 000 to 250 000 g/mol, e.g. in the range of 40 000 to 100 000 g/mol.

Examples of polylactic acid-based resins include copolymers of lactic acid and blends of polylactic acids.

If the polylactic acid-based resin is a copolymer, the polylactic acid-based resin may comprise further copolymer components in addition to lactic acid. Examples of the further copolymer component include hydroxybutyric acid, 3-hydroxybutyric acid, hydroxyvaleric acid, 3-hydroxyvaleric acid and citric acid.

The weight average molecular weight of the polylactic acid-based resin is preferably in the range of 20 000 to 400 000 g/mol, preferably in the range of 30 000 to 300 000 g/mol and most preferably in the range of 30 000 to 250 000 g/mol. Additionally or alternatively, the polylactic acid-based resin has a melt flow rate MFR (210° C.; 2.16 kg) measured according to ISO 1133 of from 1.0 to 120.0 g/10 min, preferably of from 2.0 to 100.0 g/10 min, more preferably of from 2.3 to 35.0 g/10 min and most preferably from 2.5 to 15.0 g/10 min.

In one embodiment of the present invention, the at least one hot melt extruded polymer resin, preferably the at least one hot melt extruded biodegradable and/or biocompatible polymer resin, is an aliphatic polyester selected from polyhydroxybutyrate, poly-3-hydroxybutyrate (P3HB), polyhydroxyvalerate, polyhydroxybutyrate-polyhydroxyvalerate copolymer, poly(3-hydroxybutyrate-co-3-hydroxyvalerate), and mixtures thereof.

The weight average molecular weight of the aliphatic polyester is preferably in the range of 20 000 to 400 000 g/mol, preferably in the range of 30 000 to 300 000 g/mol and most preferably in the range of 30 000 to 250 000 g/mol. Additionally or alternatively, the aliphatic polyester has a melt flow rate MFR (210° C., 2.16 kg) measured according to ISO 1133 of from 1.0 to 120.0 g/10 min, preferably of from 2.0 to 100.0 g/10 min, more preferably of from 2.3 to 35.0 g/10 min and most preferably from 2.5 to 15.0 g/10 min.

In one embodiment of the present invention, the at least one hot melt extruded polymer resin, preferably the at least one hot melt extruded biodegradable and/or biocompatible polymer resin, is a polyglyconate, poly(dioxanone) and mixtures thereof.

The weight average molecular weight of the polyglyconate and/or poly(dioxanone) is preferably in the range of 20 000 to 400 000 g/mol, preferably in the range of 30 000 to 300 000 g/mol and most preferably in the range of 30 000 to 250 000 g/mol. Additionally or alternatively, the polyglyconate and/or poly(dioxanone) has a melt flow rate MFR (210° C., 2.16 kg) measured according to ISO 1133 of from 1.0 to 120.0 g/10 min, preferably of from 2.0 to 100.0 g/10 min, more preferably of from 2.3 to 35.0 g/10 min and most preferably from 2.5 to 15.0 g/10 min.

The instant dosage form comprises the least one hot melt extruded polymer resin, preferably the at least one hot melt extruded biodegradable and/or biocompatible polymer resin, in an amount of at least 5 wt.-%, i.e. from 5 to 95 wt.-%, based on the total weight of the dosage form. Preferably, the dosage form comprises the at least one hot melt extruded polymer resin, preferably the at least one hot melt extruded biodegradable and/or biocompatible polymer resin, in an amount from 20 to 80 wt.-%, based on the total weight of the dosage form. More preferably, the dosage form comprises the at least one hot melt extruded polymer resin, preferably the at least one hot melt extruded biodegradable and/or biocompatible polymer resin, in an amount from 30 to 70 wt.-%, based on the total weight of the dosage form.

It is a further requirement of the present invention that the dosage form comprises the at least one functionalized calcium carbonate-comprising material and the at least one hot melt extruded polymer resin, preferably the at least one hot melt extruded biodegradable and/or biocompatible polymer resin, such that the weight ratio of functionalized calcium carbonate-comprising material to hot melt extruded polymer resin (FCC/polymer) ranges from 95:5 to 5:95. Preferably, the weight ratio of functionalized calcium carbonate-comprising material to hot melt extruded polymer resin (FCC/polymer) ranges from 80:20 to 20:80, more preferably from 70:30 to 30:70 and most preferably from 60:40 to 40:60. For example, the weight ratio of functionalized calcium carbonate-comprising material to hot melt extruded polymer resin (FCC/polymer) is about 50:50.

It is further required that the at least one functionalized calcium carbonate-comprising material is dispersed in the at least one hot melt extruded polymer resin, preferably the at least one hot melt extruded biodegradable and/or biocompatible polymer resin. For example, the at least one functionalized calcium carbonate-comprising material is uniformly dispersed in the at least one hot melt extruded polymer resin, preferably the at least one hot melt extruded biodegradable and/or biocompatible polymer resin.

Thus, it is appreciated that the dosage form comprises
a) at least one functionalized calcium carbonate-comprising material (FCC), preferably at least one functionalized natural and/or synthetic calcium carbonate-comprising material (FCC), which is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source,
b) at least one hot melt extruded polymer resin, preferably at least one hot melt extruded biodegradable and/or biocompatible polymer resin,
wherein the at least one functionalized calcium carbonate-comprising material is dispersed in the at least one hot melt extruded polymer resin and the weight ratio of functionalized calcium carbonate-comprising material to hot melt extruded polymer resin (FCC/polymer) ranges from 95:5 to 5:95.

In one embodiment, the dosage form consists of
a) at least one functionalized calcium carbonate-comprising material (FCC), preferably at least one functionalized natural and/or synthetic calcium carbonate-comprising material (FCC), which is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, and
b) at least one hot melt extruded polymer resin, preferably at least one hot melt extruded biodegradable and/or biocompatible polymer resin,
wherein the at least one functionalized calcium carbonate-comprising material is dispersed in the at least one hot melt extruded polymer resin and the weight ratio of functionalized calcium carbonate-comprising material to hot melt extruded polymer resin (FCC/polymer) ranges from 95:5 to 5:95.

It is preferred that the dosage form further comprises at least one active agent and/or inactive agent.

Thus, in one embodiment, the dosage form comprises, preferably consists of,
a) at least one functionalized calcium carbonate-comprising material (FCC), preferably at least one functionalized natural and/or synthetic calcium carbonate-comprising material (FCC), which is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source,
b) at least one hot melt extruded polymer resin, preferably at least one hot melt extruded biodegradable and/or biocompatible polymer resin, and
c) at least one active agent and/or inactive agent,
wherein the at least one functionalized calcium carbonate-comprising material is dispersed in the at least one hot melt extruded polymer resin and the weight ratio of functionalized calcium carbonate-comprising material to hot melt extruded polymer resin (FCC/polymer) ranges from 95:5 to 5:95.

The expression "at least one" active agent and/or inactive agent means that the dosage form comprises one or more active agent(s) and/or inactive agent(s).

According to one embodiment of the present invention, the dosage form comprises only one active agent or inactive agent. According to another embodiment of the present invention, the dosage form comprises a mixture of two or more active agent(s) and/or inactive agent(s). For example, the dosage form comprises a mixture of two or three active agent(s) and/or inactive agent(s).

Preferably, the dosage form comprises only one active agent or inactive agent.

The active agent and/or inactive agent is preferably selected from the group comprising pharmaceutically active agents, active or inactive prodrugs, nutraceuticals, food additives, cosmetic additives and mixtures thereof It is to be noted that the at least one active agent and/or inactive agent may be any such compound known to the skilled person.

The at least one pharmaceutically active agent, active or inactive prodrug is preferably selected from the group comprising pharmaceutically active agents or pharmaceutically active or inactive prodrugs of synthetic origin, semi-synthetic origin, natural origin and combinations thereof.

Thus, a pharmaceutically active agent refers to pharmaceutically active agents which are of synthetic origin, semi-synthetic origin, natural origin and combinations thereof. Further, a pharmaceutically active prodrug of the pharmaceutically active agent refers to pharmaceutically active prodrugs which are of synthetic origin, semi-synthetic origin, natural origin and combinations thereof and will be converted at a later stage to the respective pharmaceutically active agent. Further, a pharmaceutically inactive prodrug of the pharmaceutically active agent refers to pharmaceutically inactive prodrugs which are of synthetic origin, semi-synthetic origin, natural origin and combinations thereof and will be activated at a later stage to the respective pharmaceutically active agent.

The conversion or activation of such pharmaceutically active or inactive prodrugs is known to the skilled person and commonly in use, e.g. conversion and activation in the stomach and/or gastro-intestinal pathway—such as for examples by ph-mediated or enzymatic-mediated activation.

It lies within the understanding of the skilled person that the mentioned conversion and activation methods are of mere illustrative character and are not intended to be of limiting character.

It is to be noted that the at least one pharmaceutically active agents, active or inactive prodrugs thereof, may be any such compound known to the skilled person. Pharmaceutically active agents, active or inactive prodrugs thereof thus include any compound that provides prophylactic and/or therapeutic properties when administered to humans and/or animals. Examples include, but are not limited to, pharmaceutical actives, therapeutic actives, veterinarial actives, nutraceuticals, and growth regulators and the corresponding active or inactive prodrugs thereof.

For example, the at least one active agent and/or inactive agent, preferably the at least one pharmaceutically active agents, active or inactive prodrugs thereof, is an anti-tartar agent. Anti-tartar agents useful herein include phosphates. Phosphates include pyrophosphates, polyphosphates, polyphosphonates and mixtures thereof. Pyrophosphates are among the best known phosphates for use in dental care products. Pyrophosphate ions delivered to the teeth derive from pyrophosphate salts. The pyrophosphate salts useful in the present dosage form include the dialkali metal pyrophosphate salts, tetra-alkali metal pyrophosphate salts, and mixtures thereof.

Disodium dihydrogen pyrophosphate ($Na_2H_2P_2O_7$), tetrasodium pyrophosphate ($Na_4P_2O_7$), and tetrapotassium pyrophosphate ($K_4P_2O_7$) in their non-hydrated as well as hydrated forms are preferred. Anticalculus phosphates include potassium and sodium pyrophosphates; sodium tripolyphosphate; diphosphonates, such as ethane-1-hydroxy-1, I-diphosphonate; 1-azacycloheptane-1,1-diphosphonate; and linear alkyl diphosphonates; linear carboxylic acids and sodium and zinc citrate.

Agents that may be used in place of or in combination with the above pyrophosphate salt include materials such as synthetic anionic polymers including polyacrylates and copolymers of maleic anhydride or acid and methyl vinyl ether, e.g. Gantrez, as described, for example, in U.S. Pat. No. 4,627,977, to Gaffar et al. herein incorporated by reference in its entirety as to the description of such agents, as well as e.g. polyamino propane sulphonic acid (AMPS), zinc citrate trihydrate, polyphosphates, e.g. tripolyphosphate and hexametaphosphate, diphosphonates, e.g. EHDP and AMP, polypeptides, such as polyaspartic and polyglutamic acids, and mixtures thereof.

Antimicrobial agents may be also used as the at least one active agent and/or inactive agent. Such agents may include, but are not urn-ited to, 5-chloro-2-(2,4-dichlorophenoxy)-phenol, commonly referred to as triclosan, chiorhexidine, alexidine, hexetidine, sanguinarine, benzalkonium chloride, salicylamide, domiphen bromide, cetylpyridiurn chloride (CPC), tetradecyl pyridiniurn chloride (TPC); N-tetradecyl-4-ethyl pyridinium chloride (TDEPC); octenidine; delmopinol, octapinol, and other piperidino derivatives, niacin preparations; zinc/stannous ion agents; antibiotics such as AUGMENTIN, amoxycillin, tetracycline, doxycyline, minocycline, and metronidazole; and analogues, derivatives and salts of the above antimicrobial agents and mixtures thereof.

Anti-inflammatory agents may also be used as the at least one active agent and/or inactive agent, preferably the at least one pharmaceutically active agents, active or inactive prodrugs thereof. Such agents may include, but are not limited to, non-steroidal anti-inflammatory agents or NSAIDs, such as propionic acid derivatives; acetic acid derivatives; fenamic acid derivatives; biphenylcarboxylic acid derivatives; and oxicams. All of these NSAIDs are fully described in U.S. Pat. No. 4,985,459 to Sunshine et al., incorporated by reference herein in its entirety as to the description of such NSAIDs. Examples of useful NSAIDs include acetylsalicylic acid, ibuprofen, naproxen, benoxaprofen, flurbiprofen, fenoprofen, fenbufen, ketoprofen, indoprofen, pirprofen, carprofen, oxaprozin, pranoprofen, microprofen, tioxaprofen, suprofen, alminoprofen, tiaprofenic acid, fluprofen, bucloxic acid and mixtures thereof.

Also useful are the steroidal anti-inflammatory drugs such as hydrocortisone and the like, and COX-2 inhibitors such as meloxicam, celecoxib, rofecoxib, valdecoxib, etoricoxib or mixtures thereof. Mixtures of any of the above anti-inflammatories may be used.

Other materials that can be used as the at least one active agent and/or inactive agent, preferably the at least one pharmaceutically active agents, active or inactive prodrugs thereof, include commonly known mouth and throat products. These products include, but are not limited to, upper respiratory agents such as phenylephrine, diphenhydramine, dextromethorphan, bromhexine and chiorpheniramine, gastrointestinal agents such as famotidine, loperamide and simethicone, anti-fungals such as miconazole nitrate, antibiotics such as ketoprofen and fluribuprofen.

The at least one active agent and/or inactive agent may be also selected from vitamin E, i.e. tocopheroles, vitamin C, i.e. ascorbic acid and its salts, sodium pyrosulphite, butyl-hydroxytoluene, butylated hydroxyanisole; and preservatives including parabenes, benzalkonium chloride, chlorbutanol, benzyl alcohol, beta-phenylethyl alcohol, cetylpyridinium chloride, citric acid, tartaric acid, lactic acid, malic acid, acetic acid, benzoic acid, and sorbic acid and their salts; and chelating agents, such as EDTA; and gallates, such as propyl gallate.

The at least one active agent and/or inactive agent may be also selected from vitamins, such as vitamins B. C and E; minerals, such as fluorides, especially sodium fluoride, sodium monofluoro phosphate and stannous fluoride; -antiodours, such as zinc and cyclodextrins; propellants, such as 1,1,2,2-tekafluoroethane (HFC-134a), optionally being liquefied, and 1,1,1,2,3,3,3-heptafluororpropane (HFC-227), optionally being liquefied.

The at least one active agent and/or inactive agent, preferably the at least one pharmaceutically active agents, active or inactive prodrugs thereof, may be also selected from ephedrine, magaldrate, pseudoephedrine, sildenafil, xylocaine, benzalkconium chloride, caffeine, phenylephrine, amfepramone, orlistat, sibutramine, acetaminophen, aspirin, aluminium amino acetate, aluminium amino acetate in combination with magnesium oxide, aluminium oxide hydrate in combination with magnesium oxide, calcium carbonate in combination with magnesium hydroxide, calcium carbonate, dihydroxy aluminium sodium carbonate, magnesium oxide, glitazones, metformin such as metformin HCl, chlorpromazine, dimenhydrinat, domperidone, meclozine, metoclopramide, odansetron, prednisolone, promethazine, acrivastine, cetirizine, cinnarizine, clemastine, cyclizine, desloratadine, dexchlorpheniramine, dimenhydrinate, ebastine, fexofenadine, ibuprofen, levolevoproricin, loratadine, meclozine, mizolastine, promethazine, miconazole, vitamin B12, folic acid, ferro compounds, vitamin C, chlorhexidine diacetate, fluoride, decapeptide KSL, aluminium fluoride, aminochelated calcium, ammonium fluoride, ammonium fluorosilicate, ammonium monofluorophosphate, calcium fluoride, calcium gluconate, calcium glycerophosphate, calcium lactate, calcium monofluorophosphate, calciumcarbonate, carbamide, cetyl pyridinium chloride, chlorhexidine, chlorhexidine digluconate, chlorhexidine chloride, chlorhexidine diacetate, CPP caseine phospho peptide, hexetedine, octadecentyl ammonium fluoride, potassium fluorosilicate, potassium Chloride, potassium monofluorophosphate, sodium bi carbonate, sodium carbonate, sodium fluoride, sodium fluorosilicate, sodium monofluorophosphate, sodium tri polyphosphate, stannous fluoride, stearyl trihydroxyethyl propylenediamine dihydrofluoride, strontium chloride, tetra potassium pyrophosphate, tetra sodium pyrophosphate, tripotassium orthophosphate, trisodium orthophosphate, alginic acid, aluminium hydroxide, sodium bicarbonate, sildenafil, tadalafil, vardenafil, yohimbine, cimetidine, nizatidine, ranitidine, acetylsalicylic acid, clopidogrel, acetylcysteine, bromhexine, codeine, dextromethorphan, diphenhydramine, noscapine, phenylpropanolamine, vitamin D, simvastatin, bisacodyl, lactitol, lactulose, magnesium oxide, sodium picosulfate, senna glycosides, benzocaine, lidocaine, tetracaine, almotriptan, eletriptan, naratriptan, rizatriptan, sumatriptan, zolmitriptan, calcium, chromium, copper, iodine, iron, magnesium, manganese, molybdenium, phosphor, selenium, zinc, chloramine, hydrogenperoxide, metronidazole, triamcinolonacetonide, benzethonium chl., cetyl pyrid. chl., chlorhexidine, fluoride, lidocaine, amphotericin, miconazole, nystatin, fish oil, *Ginkgo biloba*, ginseng, ginger, purple coneflower, saw palmetto, cetirizine, levocetirizine, loratadine, diclofenac, flurbiprofen, acrivastine pseudoephedrine, loratadine pseudoephedrine, glucosamine, hyaluronic acid, decapeptide KSL-W, decapeptide KSL, resveratrol, misoprostol, bupropion, ondansetron HCl, esomeprazole, lansoprazole, omeprazole, pantoprazole, rabeprazole, bacteria and the like, loperamide, simethicone, acetylsalicylic acid and others, sucralfate, vitamin A, vitamin B1, vitamin B12, vitamin B2, vitamin B6, biotin, vitamin C, vitamin D, vitamin E, folinic acid, vitamin K, niacin, Q10, clotrimazole, fluconazole, itraconazole, ketoconazole, terbinafine, allopurinol, probenecid, atorvastatin, fluvastatin, lovastatin, nicotinic acid, pravastatin, rosuvastatin, simvastatin, pilocarpine, naproxen, alendronate, etidronate, raloxifene, risedronate, benzodiazepines, disulfiram, naltrexone, buprenorphine, codeine, dextropropoxyphene, fentanyl, hydromorphone, ketobemidone, ketoprofen, methadone, morphine, naproxen, nicomorphine, oxycodone, pethidine, tramadol, amoxicillin, ampicillin, azithromycin, ciprofloxacin, clarithromycin, doxycyclin, erythromycin, fusidic acid, lymecycline, metronidazole, moxifloxacin, ofloxacin, oxytetracycline, phenoxymethylpenicillin, rifamycins, roxithromycin, sulfamethizole, tetracycline, trimethoprim, vancomycin, acarbose, glibenclamide, gliclazide, glimepiride, glipizide, insulin, repaglinide, tolbutamide, oseltamivir, aciclovir, famciclovir, penciclovir, valganciclovir, amlopidine, diltiazem, felodipine, nifedipine, verapamil, finasteride, minoxidil, cocaine, buphrenorphin, clonidine, methadone, naltrexone, calcium antagonists, clonidine, ergotamine, β-blockers, aceclofenac, celecoxib, dexiprofen, etodolac, indometacin, ketoprofen, ketorolac, lomoxicam, meloxicam, nabumetone, oiroxicam, parecoxib, phenylbutazone, piroxicam, tiaprofenic acid, tolfenamic acid, aripiprazole, chlorpromazine, chlorprothixene, clozapine, flupentixol, fluphenazine, haloperidol, lithium carbonate, lithium citrate, melperone, penfluridol, periciazine, perphenazine, pimozide, pipamperone, prochlorperazine, risperidone, thioridizin, fluconazole, itraconazole, ketoconazole, voriconazole, opium, benzodiazepines, hydroxine, meprobamate, phenothiazine, aluminiumaminoacetate, esomeprazole, famotidine, magnesium oxide, nizatide, omeprazole, pantoprazole, fluconazole, itraconazole, ketoconazole, metronidazole, amphetamine, atenolol, bisoprolol fumarate, metoprolol, metropolol, pindolol, propranolol, auranofin, and bendazac.

Further examples of useful at least one active agent and/or inactive agent, preferably the at least one pharmaceutically active agents, active or inactive prodrugs thereof, include agents selected from the therapeutical groups comprising: Analgesic, Anaestetic, Antipyretic, Anti allergic, Anti-arrhythmic, Appetite suppressant, Antifungal, Anti-inflammatory, Broncho dilator, Cardiovascular drugs, Coronary dilator, Cerebral dilator, Peripheral vasodilator, Anti-infective, Psychotropic, Anti-manic, Stimulant, Antihistamine, Laxative, Decongestrant, Gastro-intestinal sedative, Sexual dysfunction agent, Desinfectants, Anti-diarrheal, Anti-anginal substance, Vasodilator, Anti-hypertensive agent, Vasoconstrictor, Migraine treating agent, Antibiotic, Tranquilizer, Antipsychotic, Anti-tumour drug, Anticoagulant, Antithrombotic agent, Hypnotic, Sedative, Anti-emetic, Anti-, nauseant, Anticonvulsant, Neuromuscular agent, Hyper and hypoglycaemic, Thyroid and antithyroid, Diuretic, Antispasmodic, Uterine relaxant, Anti-obesity agent, Anoretic, Spasnolytics, Anabolic agent, Erythropoietic agent, Anti-asthmatic, Expectorant, Cough suppressant, Mucolytic, Anti-uricemic agent, Dental vehicle, Breath freshener, Antacid, Anti-diuretc, Anti-flatulent, Betablokker, Teeth Whitener, Enzyme, Co-enzyme, Protein, Energy booster, Fibre, Probiotics, Prebiotics, Antimicrobial agent, NSAID, Anti-tussives, Decongestrants, Anti-histamines, Expectorants, Anti-diarrheals, Hydrogen antagonists, Proton pump inhibitors, General nonselective CNS depressants, General nonselective CNS stimulants, Selectively CNS function modifying drugs, Antiparkinsonism, Narcotic-analgetics, Analgetic-antipyretics, Psychopharmacological drugs, and Sexual dysfunction agents.

Examples of useful at least one active agent and/or inactive agent may also include: Casein glyco-macro-peptide (CGMP), Triclosan, Cetyl pyridinium chloride, Domiphen bromide, Quarternary ammonium salts, zinc components, Sanguinarine, Fluorides, Alexidine, Octonidine, EDTA, Aspirin, Acetaminophen, Ibuprofen, Ketoprofen, Diflunisal, Fenoprofen calcium, Naproxen, Tolmetin sodium, Indomethacin, Benzonatate, Caramiphen edisylate, Menthol, Dextromethorphan hydrobromide, Theobromine hydrochloride, Chlophendianol Hydrochloride, Pseudoephedrine Hydrochloride, Phenylephrine, Phenylpropanolamine, Pseudoephedrine sulphate, Brompheniramine maleate, Chlorpheniramine-maleate, Carbinoxamine maleate, Clemastine fumarate, Dexchlorpheniramine maleate, Dephenhydramine hydrochloride, Diphenpyralide hydrochloride, Azatadine maleate, Diphenhydramine citrate, Doxylamine succinate, Promethazine hydrochloride, Pyrilamine maleate, Tripellenamine citrate, Triprolidine hydrochloride, Acrivastine, Loratadine, Brompheniramine, Dexbrompheniamine, Guaifenesin, Ipecac, potassium iodide, Terpin hydrate, Loperamide, Famotidine, Ranitidine, Omeprazole, Lansoprazole, Aliphatic alcohols, Barbiturates, caffeine, ctrychnine, Picrotoxin, Pentyenetetrazol, Phenyhydantoin, Phenobarbital, Primidone, Carbamazapine, Etoxsuximide, Methsuximide, Phensuximide, Trimethadione, Diazepam, Benzodiazepines, Phenacemide, Pheneturide, Acetazolamide, Sulthiame, bromide, Levodopa, Amantadine, Morphine, Heroin, Hydromorphone, Metopon, Oxymorphone, Levophanol, Codeine, Hydrocodone, Xycodone, Nalorphine, Naloxone, Naltrexone, Salicylates, Phenylbutazone, Indomethacin, Phenacetin, Chlorpromazine, Methotrimeprazine, Haloperidol, Clozapine, Reserpine, Imipramine, Tranylcypromine, Phenelzine, Lithium, Sildenafil citrate, Tadalafil, and Vardenafil CL.

Examples of useful at least one active agent and/or inactive agent may include active ingredients selected from the groups of ace-inhibitors, antianginal drugs, anti-arrhythmias, anti-asthmatics, anti-cholesterolemics, analgesics, anesthetics, anticonvulsants, anti-depressants, anti-diabetic agents, anti-diarrhea preparations, antidotes, anti-histamines, anti-hypertensive drugs, anti-inflammatory agents, anti-lipid agents, anti-manics, anti-nauseants, anti-stroke agents, anti-thyroid preparations, anti-tumour drugs, anti-viral agents, acne drugs, alkaloids, amino acid preparations, anti-tussives, anti-uricemic drugs, anti-viral drugs, anabolic preparations, systemic and non-systemic anti-infective agents, anti-neoplasties, antiparkinsonian agents, anti-rheumatic agents, appetite stimulants, biological response modifiers, blood modifiers, bone metabolism regulators, cardiovascular agents, central nervous system stimulates, cholinesterase inhibitors, contraceptives, decongestants, dietary supplements, dopamine receptor agonists, endometriosis management agents, enzymes, erectile dysfunction therapies such as sildenafil citrate, which is currently marketed as Viagra™, fertility agents, gastrointestinal agents, homeopathic remedies, hormones, hypercalcemia and hypocalcemia management agents, immunomodulators, immunosuppressives, migraine preparations, motion sickness treatments, muscle relaxants, obesity management agents, osteoporosis preparations, oxytocics, parasympatholytics, parasympathomimetics, prostaglandins, psychotherapeutic agents, respiratory agents, sedatives, smoking cessation aids such as bromocriptine, sympatholytics, tremor preparations, urinary tract agents, vasodilators, laxatives, antacids, ion exchange resins, anti-pyretics, appetite suppressants, expectorants, anti-anxiety agents, anti-ulcer agents, anti-inflammatory substances, coronary dilators, cerebral dilators, peripheral vasodilators, psycho-tropics, stimulants, anti-hypertensive drugs, vasoconstrictors, migraine treatments, antibiotics, tranquilizers, anti-psychotics, anti-tumour drugs, anti-coagulants, anti-thrombotic drugs, hypnotics, anti-emetics, anti-nauseants, anti-convulsants, neuromuscular drugs, hyper- and hypo-glycemic agents, thyroid and anti-thyroid preparations, diuretics, anti-spasmodics, terine relaxants, anti-obesity drugs, erythropoietic drugs, anti-asthmatics, cough suppressants, mucolytics, DNA and genetic modifying drugs, and combinations thereof.

Examples of useful at least one active agent and/or inactive agent contemplated for use in the present dosage form can include antacids, H2-antagonists, and analgesics. For example, antacid dosages can be prepared using the ingredients calcium carbonate alone or in combination with magnesium hydroxide, and/or aluminium hydroxide. Moreover, antacids can be used in combination with H2-antagonists. Analgesics include opiates and opiate derivatives, such as Oxycontin™, ibuprofen, aspirin, acetaminophen, and combinations thereof that may optionally include caffeine.

Other useful at least one active agent and/or inactive agent for use in embodiments can include anti-diarrheals such as Immodium™ AD, anti-histamines, anti-tussives, decongestants, vitamins, and breath fresheners. Also contemplated for use herein are anxiolytics such as Xanax™; anti-psychotics such as Clozaril™ and Haldol™; non-steroidal anti-inflammatories (NSAID's) such as ibuprofen, naproxen sodium, Voltaren™ and Lodine™, anti-histamines such as Claritin™, Hismanal™ Relafen™, and Tavist™; antiemetics such as Kytril™ and Cesamet™; bronchodilators such as Bentolin™, Proventil™; anti-depressants such as Prozac™ Zoloft™, and Paxil™; anti-migraines such as Imigra™, ACE-inhibitors such as Vasotec™, Capoten™ and Zestril™; anti-Alzheimer's agents, such as Nicergoline™; and CaH-antagonists such as Procardia™, Adalat™, and Calan™.

The popular H2-antagonists which are contemplated for use in the present invention include cimetidine, ranitidine hydrochloride, famotidine, nizatidien, ebrotidine, mifentidine, roxatidine, pisatidine and aceroxatidine.

Active antacid ingredients can include, but are not limited to, the following: aluminium hydroxide, dihydroxyaluminium aminoacetate, aminoacetic acid, aluminium phosphate, dihydroxyaluminium sodium carbonate, bicarbonate, bismuth aluminate, bismuth carbonate, bismuth subcarbonate, bismuth subgallate, bismuth subnitrate, bismuth subsilysilate, calcium phosphate, citrate ion (acid or salt), amino acetic acid, hydrate magnesium aluminate sulfate, magaldrate, magnesium aluminosilicate, magnesium carbonate, magnesium glycinate, magnesium hydroxide, magnesium oxide, magnesium trisilicate, milk solids, aluminium mono- or dibasic calcium phosphate, tricalcium phosphate, potassium bicarbonate, sodium tartrate, sodium bicarbonate, magnesium aluminosilicates, tartaric acids and salts.

A variety of nutraceuticals may also be used as the at least one active agent and/or inactive agent including virtually any vitamin or mineral. For example, vitamin A, vitamin C, vitamin D, vitamin E, vitamin K, vitamin B6, vitamin B12, thiamine, riboflavin, biotin, folic acid, niacin, pantothenic acid, sodium, potassium, calcium, magnesium, phosphorus, sulfur, chlorine, iron, copper, iodine, zinc, selenium, manganese, choline, chromium, molybdenum, fluorine, cobalt and combinations thereof, may be used. Examples of nutraceuticals that can be used as at least one active agent and/or inactive agent are set forth in U.S. Patent Application Publication Nos. 2003/0157213 A1, 2003/0206993 and 2003/0099741 A1 which are incorporated in their entirety herein by reference for all purposes. Various herbals may also be used as the at least one active agent and/or inactive agent such as those with various medicinal or dietary supplement properties. Herbals are generally aromatic plants or plant parts and or extracts thereof that can be used medicinally or for flavoring. Suitable herbals can be used singly or in various mixtures. Commonly used herbs include Echinacea, Goldenseal, Calendula, Rosemary, Thyme, Kava Kava, Aloe, Blood Root, Grapefruit Seed Extract, Black Cohosh, Ginseng, Guarana, Cranberry, Ginko Biloba, St. John's Wort, Evening Primrose Oil, Yohimbe Bark, Green Tea, Ma Huang, Maca, Bilberry, Lutein, and combinations thereof.

In some embodiments the at least one active agent and/or inactive agent can include but is not limited to L-carnitine, choline, coenzyme Q10, alpha-lipoic acid, omega-3-fatty acids, pepsin, phytase, trypsin, lipases, proteases, cellulases, and combinations thereof.

The at least one active agent and/or inactive agent can also include ascorbic acid, citric acid, rosemary oil, vitamin A, vitamin E, vitamin E phosphate, tocopherols, di-alpha-tocopheryl phosphate, tocotrienols, alpha lipoic acid, dihydrolipoic acid, xanthophylls, beta cryptoxanthin, lycopene, lutein, zeaxanthin, astaxanthin, beta-carotene, carotenes, mixed carotenoids, polyphenols, flavonoids, and combinations thereof.

In some embodiments, the at least one active agent and/or inactive agent can be selected from phytochemicals such as cartotenoids, chlorophyll, chlorophyllin, fibre, flavanoids, anthocyanins, cyaniding, delphinidin, malvidin, pelargonidin, peonidin, petunidin, flavanols, catechin, epicatechin, epigallocatechin, epigallocatechingallate, theaflavins, thearubigins, proanthocyanins, flavonols, quercetin, kaempferol, myricetin, isorhamnetin, flavononeshesperetin, naringenin, eriodictyol, tangeretin, flavones, apigenin, luteolin, lignans, phytoestrogens, resveratrol, isoflavones, daidzein, genistein, glycitein, soy isoflavones, and combinations thereof.

In some embodiments, the at least one active agent and/or inactive agent can be selected from analgesics/anesthetics such as menthol, phenol, hexylresorcinol, benzocaine, dyclonine hydrochloride, benzyl alcohol, salicyl alcohol, and combinations thereof. In some embodiments, the at least one active agent and/or inactive agent can be selected from demulcents such as slippery elm bark, pectin, gelatin, and combinations thereof. In some embodiments, the at least one active agent and/or inactive agent can be selected from antiseptic ingredients such as cetylpyridinium chloride, domiphen bromide, dequalinium chloride, and combinations thereof.

In some embodiments, the at least one active agent and/or inactive agent can be selected from antitussive ingredients such as chlophedianol hydrochloride, codeine, codeine phosphate, codeine sulfate, dextromethorphan, dextromethorphan hydrobromide, diphenhydramine citrate, and diphenhydramine hydrochloride, and combinations thereof.

In some embodiments, the at least one active agent and/or inactive agent can be selected from throat soothing agents such as honey, propolis, aloe vera, glycerine, menthol and combinations thereof can be included. In still other embodiments, at least one active agent and/or inactive agent can be selected from cough suppressants. Such cough suppressants can fall into two groups: those that alter the texture or production of phlegm such as mucolytics and expectorants; and those that suppress the coughing reflex such as codeine (narcotic cough suppressants), antihistamines, dextromethorphan and isoproterenol (non-narcotic cough suppressants). In some embodiments, ingredients from either or both groups can be included.

In still other embodiments, the at least one active agent and/or inactive agent can be an antitussive selected from the group comprising codeine, dextromethorphan, dextrorphan, diphenhydramine, hydrocodone, noscapine, oxycodone, pentoxyverine and combinations thereof. In some embodiments, the at least one active agent and/or inactive agent can be selected from antihistamines such as acrivastine, azatadine, brompheniramine, chlo[phi]heniramine, clemastine, cyproheptadine, dexbrompheniramine, dimenhydrinate, diphenhydramine, doxylamine, hydroxyzine, meclizine, phenindamine, phenyltoloxamine, promethazine, pyrilamine, tripelennamine, triprolidine and combinations thereof. In some embodiments, the at least one active agent and/or inactive agent can be selected from non-sedating antihistamines such as astemizole, cetirizine, ebastine, fexofenadine, loratidine, terfenadine, and combinations thereof.

In some embodiments, the at least one active agent and/or inactive agent can be selected from expectorants as ammonium chloride, guaifenesin, ipecac fluid extract, potassium iodide and combinations thereof. In some embodiments, the at least one active agent and/or inactive agent can be selected from mucolytics such as acetylcycsteine, ambroxol, bromhexine and combinations thereof. In some embodiments, the at least one active agent and/or inactive agent can be selected from analgesic, antipyretic and anti-inflammatory agents such as acetaminophen, aspirin, diclofenac, diflunisal, etodolac, fenoprofen, flurbiprofen, ibuprofen, ketoprofen, ketorolac, nabumetone, naproxen, piroxicam, caffeine and mixtures thereof. In some embodiments, the at least one active agent and/or inactive agent can be selected from local anesthetics such as lidocaine, benzocaine, phenol, dyclonine, benzonotate and mixtures thereof. In some embodiments, the at least one active agent and/or inactive agent can be selected from nasal decongestants and ingredients that provide the perception of nasal clearing. In some embodiments, such as nasal decongestants can include but are not limited to phenylpropanolamine, pseudoephedrine, ephedrine, phenylephrine, oxymetazoline, and combinations thereof. In some embodiments, the at least one active agent and/or inactive agent can be selected from ingredients that provide a perception of nasal clearing such as menthol, camphor, borneol, ephedrine, eucalyptus oil, peppermint oil, methyl salicylate, bornyl acetate, lavender oil, wasabi extracts, horseradish extracts, and combinations thereof. In some embodiments, a perception of nasal clearing can be provided by odoriferous essential oils, extracts from woods, gums, flowers and other botanicals, resins, animal secretions, and synthetic aromatic materials.

For example, the at least one active agent and/or inactive agent is metformin HCl.

It is appreciated that the at least one active agent and/or inactive agent is/are preferably loaded onto or mixed with the at least one functionalized calcium carbonate-comprising material (FCC). That is to say, the at least one functionalized calcium carbonate-comprising material preferably comprises the at least one active agent and/or inactive agent on its accessible surface area. The term "accessible" surface area of a material refers to the part of the material surface which is in contact with the at least one active agent and/or inactive agent during loading or mixing.

Additionally or alternatively, the at least one active agent and/or inactive agent is/are preferably dispersed in the at least one hot melt extruded polymer resin comprising the at least one functionalized calcium carbonate-comprising material (FCC). That is to say, the at least one active agent and/or inactive agent is dispersed in the at least one hot melt extruded polymer resin independent from the at least one functionalized calcium carbonate-comprising material. For example, the at least one active agent and/or inactive agent is/are preferably uniformly dispersed in the at least one hot melt extruded polymer resin comprising the at least one functionalized calcium carbonate-comprising material (FCC).

In one embodiment, the at least one active agent and/or inactive agent is/are loaded onto or mixed with the at least one functionalized calcium carbonate-comprising material (FCC) and the at least one active agent and/or inactive agent is/are dispersed in the at least one hot melt extruded polymer resin comprising the at least one functionalized calcium carbonate-comprising material (FCC). It is appreciated that the at least one active agent and/or inactive agent loaded onto or mixed with the at least one functionalized calcium carbonate-comprising material (FCC) and dispersed in the at least one hot melt extruded polymer resin may be the same or different.

Additionally or alternatively, the at least one active agent and/or inactive agent is/are in form of a core which is at least partially covered by the at least one hot melt extruded polymer resin comprising the at least one functionalized calcium carbonate-comprising material (FCC). In this embodiment, the at least one active agent and/or inactive agent is/are preferably in form of a compacted tablet. It is appreciated that this arrangement is especially preferred if a tablet-in-cup is prepared.

In one embodiment, the at least one active agent and/or inactive agent is/are in form of a core which is at least partially covered by the at least one hot melt extruded polymer resin comprising the at least one functionalized calcium carbonate-comprising material (FCC) and the at least one active agent and/or inactive agent is/are loaded onto or mixed with the at least one functionalized calcium carbonate-comprising material (FCC). It is appreciated that the at least one active agent and/or inactive agent loaded onto or mixed with the at least one functionalized calcium carbonate-comprising material (FCC) and being in form of a core may be the same or different.

Additionally or alternatively, the at least one active agent and/or inactive agent is/are in form of a layer which at least partially covers a core made from the at least one hot melt extruded polymer resin comprising the at least one functionalized calcium carbonate-comprising material (FCC). In this embodiment, the core is preferably a compacted tablet.

In one embodiment, the at least one active agent and/or inactive agent is/are in form of a layer which at least partially covers a core made from the at least one hot melt extruded polymer resin comprising the at least one functionalized calcium carbonate-comprising material (FCC) and the at least one active agent and/or inactive agent is/are loaded onto or mixed with the at least one functionalized calcium carbonate-comprising material (FCC). It is appreciated that the at least one active agent and/or inactive agent loaded onto or mixed with the at least one functionalized calcium carbonate-comprising material (FCC) and being in form of a layer at least partially covering a core may be the same or different.

Additionally or alternatively, the at least one active agent and/or inactive agent is/are in form of a layered structure of at least two layers, wherein at least one layer is made from the hot melt extruded polymer resin comprising the at least one functionalized calcium carbonate-comprising material (FCC).

In one embodiment, the at least one active agent and/or inactive agent is/are in form of a layered structure of at least two layers, wherein at least one layer is made from the hot melt extruded polymer resin comprising the at least one functionalized calcium carbonate-comprising material (FCC) and the at least one active agent and/or inactive agent is/are loaded onto or mixed with the at least one functionalized calcium carbonate-comprising material (FCC). It is appreciated that the at least one active agent and/or inactive agent loaded onto or mixed with the at least one functionalized calcium carbonate-comprising material (FCC) and being in form of a layered structure may be the same or different.

It is preferred that the dosage form further comprises at least one excipient.

Thus, in one embodiment, the dosage form comprises, preferably consists of,
a) at least one functionalized calcium carbonate-comprising material (FCC), preferably at least one functionalized natural and/or synthetic calcium carbonate-comprising material (FCC), which is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source,
b) at least one hot melt extruded polymer resin, preferably at least one hot melt extruded biodegradable and/or biocompatible polymer resin, and
c) at least one excipient,
wherein the at least one functionalized calcium carbonate-comprising material is dispersed in the at least one hot melt extruded polymer resin and the weight ratio of functionalized calcium carbonate-comprising material to hot melt extruded polymer resin (FCC/polymer) ranges from 95:5 to 5:95.

For example, the dosage form comprises, preferably consists of,
a) at least one functionalized calcium carbonate-comprising material (FCC), preferably at least one functionalized natural and/or synthetic calcium carbonate-comprising material (FCC), which is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source,
b) at least one hot melt extruded polymer resin, preferably at least one hot melt extruded biodegradable and/or biocompatible polymer resin,
c) at least one active agent and/or inactive agent, and
d) at least one excipient,
wherein the at least one functionalized calcium carbonate-comprising material is dispersed in the at least one hot melt extruded polymer resin and the weight ratio of functionalized calcium carbonate-comprising material to hot melt extruded polymer resin (FCC/polymer) ranges from 95:5 to 5:95.

The expression "at least one" excipient means that the dosage form comprises one or more excipient(s).

According to one embodiment of the present invention, the dosage form comprises only one excipient. According to another embodiment of the present invention, the dosage form comprises a mixture of two or more excipient(s). For example, the dosage form comprises a mixture of two or three excipient(s).

Preferably, the dosage form comprises only one excipient.

For example, the at least one excipient is selected from the group comprising disintegrants, lubricants, inner-phase lubricants, outer-phase lubricants, impact modifiers, plasticizers, waxes, stabilizers, pigments, coloring agents, scenting agents, taste masking agents, flavoring agents, sweeteners, mouth-feel improvers, binders, diluents, film forming agents, adhesives, buffers, adsorbents, odour-masking agents and mixtures thereof.

It lies within the understanding of the skilled person that the mentioned excipients are of mere illustrative character and are not intended to be of limiting character.

Preferably, the dosage form according to the present invention comprises at least one disintegrant selected form the group comprising modified cellulose gums, insoluble cross-linked polyvinylpyrrolidones, starch glycolates, micro crystalline cellulose, pregelatinized starch, sodium carboxymethyl starch, low-substituted hydroxypropyl cellulose, homopolymers of N-vinyl-2-pyrrolidone, alkyl-,hydroxyalkyl-, carboxyalkyl-cellulose esters, alginates, microcrystalline cellulose and its polymorphic forms, ion exchange resins, gums, chitin, chitosan, clays, gellan gum, crosslinked polacrillin copolymers, agar, gelatine, dextrines, acrylic acid polymers, carboxymethylcellulose sodium/calcium, hydroxpropyl methyl cellulose phtalate, shellac or mixtures thereof.

Examples of suitable disintegrants are: Ac-Di-Sol®, FMC, USA—which is a modified cellulose gum; Kollidon®CL, BASF, Germany—which is an insoluble crosslinked polyvinlypyrrolidone; Vivastar®, JRS, Germany—which is a sodium starch glycolate; MCC Polymorph II (MCC SANAQ Burst®)—Pharmatrans Sanaq AG, Switzerland—which is a stable crystal polymorph type II of Microcrystalline cellulose, MCC SANAQ 102 as standard microcrystalline cellulose (MCC).

In one embodiment, the at least one excipient is a lubricant, preferably an inner-phase lubricant and/or outer-phase lubricant, preferably at least one inner-phase lubricant. Alternatively, the at least one excipient is at least one inner-phase lubricant and outer-phase lubricant.

Said at least one inner-phase lubricant can be selected from the group comprising sorbitan esters of fatty acids and polyoxyethylated hydrogenated castor oil (e.g. the product sold under the trade name CREMOPHOR®), block copolymers of ethylene oxide and propylene oxide (e.g. products sold under trade names PLURONIC® and POLOXAMER®), polyoxyethylene fatty alcohol ethers, polyoxyethylene sorbitan fatty acid esters, sorbitan esters of fatty acids and polyoxyethylene steraric acid esters, stearyl alcohol, glycerol dibehenate, sodium stearyl fumarate, glycerol distearate and combinations thereof. Preferably, said at least one inner-phase lubricant is sodium stearyl fumarate.

Said at least one outer-phase lubricant can be selected from the group comprising lecithin, polyoxyethylene stearate, polyoxyethylene sorbitan fatty acid esters, fatty acid salts, mono and diacetyl tartaric acid esters of mono and diglycerides of edible fatty acids, citric acid esters of mono and diglycerides of edible fatty acids, saccharose esters of fatty acids, polyglycerol esters of fatty acids, polyglycerol esters of interesterified castor oil acid (E476), sodium stearoyllactylate, magnesium and/or calcium stearate, hydrogenated vegetable oils, stearic acid, sodium lauryl sulphate, magnesium lauryl sulphate, colloidal silica, talc and combinations thereof. Preferably, said at least one outer-phase lubricant is magnesium and/or calcium stearate, more preferably magnesium stearate.

In one embodiment, the at least one excipient is a plasticizer. It is appreciated that plasticizers lower the melting point of the polymer for the hot melt extrusion process and thus may be advantageously used for preparing the hot melt extruded polymer resin. For example, the plasticizer can be a citrate-based plasticizer selected from the group consisting of triethyl citrate (TEC), tributyl citrate (TBC), acetyl tributyl citrate (ATBC), acetyl triethyl citrate (ATEC), monoglycerides, acetylated monoglycerides and acetyl tri 2-ethyl-hexyl citrate (ATEHC).

According to a further embodiment of the present dosage form, the at least one excipient may be further selected from binders, diluents, film forming agents, adhesives, buffers, adsorbents, natural or synthetic scenting agents, natural or synthetic flavouring agents, natural or synthetic coloring agents, natural or synthetic sweeteners, natural or synthetic odour-masking agents, natural or synthetic flavouring- or taste-masking agents, natural and/or synthetic mouthfeel improvers and mixtures thereof.

Suitable natural or synthetic scenting agents include one or more volatilized chemical compounds, generally at a very low concentration, that humans or other animals perceive by the sense of olfaction.

Suitable natural or synthetic flavoring agents include but are not limited to mints, such as peppermint, menthol, vanilla, cinnamon, various fruit flavors, both individual or mixed, essential oils such as thymol, eucalyptol, menthol, and methyl salicylate, allylpyrazine, methoxypyrazines, 2-isobutyl-3 methoxypyrazine, acetyl-L-pyrazines, 2-acetoxy pyrazine, aldehydes, alcohols, esters, ketones, pyrazines, phenolics, terpenoids and mixtures thereof.

The flavoring agents are generally utilized in amounts that will vary depending upon the individual flavor, and may, for example, range in amount of about 0.5% to about 4% by weight of the final dosage form.

Suitable natural or synthetic coloring agents include, but are not limited to, titanium dioxide, flavone dyes, isoquinoline dyes, polyene colorants, pyran colorants, naphthochinone dyes, chinone and anthrachinone dyes, chromene dyes, benzophyrone dyes as well as indigoid dyes and indole colorants. Examples thereof are caramel coloring, annatto, chlorophyllin, cochineal, betanin, turmeric, saffron, paprika, lycopene, pandan and butterfly pea.

Suitable natural or synthetic sweeteners include but are not limited to xylose, ribose, glucose, mannose, galactose, fructose, dextrose, sucrose, sugar, maltose, partially hydrolyzed starch, or corn syrup solid, and sugar alcohols such as sorbitol, xylitol, mannitol, and mixtures thereof; water soluble artificial sweeteners such as the soluble saccharin salts, i.e. sodium, or calcium saccharin salts, cyclamate salts, acesulfam-K and the like, and the free acid form of saccharin and aspartame based sweeteners such as L-aspartyl-phenyl-alanine methyl ester, Alitame® or Neotame®.

In general, the amount of sweetener will vary with the desired amount of sweeteners selected for a particular dosage form composition.

Suitable natural and/or synthetic mouthfeel improvers comprise but are not limited to polyethylenoxide (PEO-1NF), provided by Sumitomo Seika, Osaka, Lot.L20141017A, Hydroxylpropylcellulose (L-HPC LH-11), Shin-Etsu, Japan, Lot.505200, Hydroxypropylethylcellulose (Methocel E15 LV Premium EP), Lot. LD250012N23, Gummi arabicum Pheur, Roth, Germany, Lot.024208213, or Instant gum AA, Nexira, France or combinations thereof.

The total amount of the at least one excipient in the dosage form is preferably in the range from about 0.1 wt.-% to about 10.0 wt.-%, preferably from about 0.3 wt.-% to about 5.0 wt.-%, more preferably from about 0.5 wt.-% to about 2.5 wt.-% based on the total weight of the dosage form.

The at least one excipient is preferably dispersed in the at least one hot melt extruded polymer resin comprising the at least one functionalized calcium carbonate-comprising material (FCC). That is to say, the at least one excipient is preferably dispersed in the at least one hot melt extruded polymer resin independent from the at least one functionalized calcium carbonate-comprising material. For example, the at least one excipient is uniformly dispersed in the at least one hot melt extruded polymer resin comprising the at least one functionalized calcium carbonate-comprising material (FCC).

Additionally or alternatively, the at least one excipient is present in a core, preferably a compacted tablet, which is at least partially covered by the at least one hot melt extruded polymer resin comprising the at least one functionalized calcium carbonate-comprising material (FCC). In one embodiment, also the layer at least partially covering the core comprises at least one excipient. It is appreciated that the at least one excipient in the core and the layer at least partially covering the core may be the same or different.

Alternatively, the at least one excipient is present in a layer which at least partially covers a core, preferably a compacted tablet, made from the at least one hot melt extruded polymer resin comprising the at least one functionalized calcium carbonate-comprising material (FCC). In one embodiment, also the core made from the at least one hot melt extruded polymer resin comprises at least one excipient. It is appreciated that the at least one excipient in the core and the layer at least partially covering the core may be the same or different.

Alternatively, the at least one excipient is present in a layered structure of at least two layers, wherein at least one layer comprises the at least one excipient.

The dosage form of the present invention is in form of powder, tablets such as multi-layered tablets, tablets of altered geometric configuration or matrix-tablets, mini-tablets, pellets, capsules, granules and/or a tablet-in-cup.

Such dosage forms and their configuration are well known in the art, for example, from Kovanya Moodley, et al. "Oral drug delivery systems comprising altered geometric configurations for controlled drug delivery"; Int. J. Mol. Sci. 2012, 13, 18-43, which is thus herein incorporated by reference in its entirety.

The inventors surprisingly found out that the dosage form of the present invention is lighter and less voluminous at higher drug load, especially compared to a conventional dosage form comprising a functionalized calcium carbonate-comprising material.

The present invention is further related to the use of the dosage form in pharmaceutical, nutraceutical, cosmetic, home and personal care products. Particularly, to the use of the dosage form, which is in form of powder, tablets such as multi-layered tablets, tablets of altered geometric configuration or matrix-tablets, mini-tablets, pellets, capsules, granules and/or a tablet-in-cup, in pharmaceutical, nutraceutical, cosmetic, home and personal care products.

The present invention is further related to a pharmaceutical, nutraceutical, cosmetic, home and personal care product comprising the dosage form. Particularly, the dosage form is in form of powder, tablets such as multi-layered tablets, tablets of altered geometric configuration or matrix-tablets, mini-tablets, pellets, capsules, granules and/or a tablet-in-cup.

According to one aspect of the present invention a tablet-in cup is provided comprising
   a) at least one functionalized calcium carbonate-comprising material (FCC), which is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source,
   b) at least one hot melt extruded polymer resin,
   wherein the at least one functionalized calcium carbonate-comprising material is dispersed in the at least one hot melt extruded polymer resin and the weight ratio of functionalized calcium carbonate-comprising material to hot melt extruded polymer resin (FCC/polymer) ranges from 95:5 to 5:95.

In one embodiment, the dosage form comprises, preferably consists of,
   a) at least one functionalized calcium carbonate-comprising material (FCC), preferably at least one functionalized natural and/or synthetic calcium carbonate-comprising material (FCC), which is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source,
   b) at least one hot melt extruded polymer resin, preferably at least one hot melt extruded biodegradable and/or biocompatible polymer resin, and
   c) at least one active and/or inactive agent,
   d) optionally at least one excipient,
   wherein the at least one functionalized calcium carbonate-comprising material is dispersed in the at least one hot melt extruded polymer resin and the weight ratio of functionalized calcium carbonate-comprising material to hot melt extruded polymer resin (FCC/polymer) ranges from 95:5 to 5:95.

For example, the at least one active agent and/or inactive agent is/are in form of a core which is at least partially covered by the at least one hot melt extruded polymer resin comprising the at least one functionalized calcium carbonate-comprising material (FCC). In this embodiment, the at least one active agent and/or inactive agent is/are preferably in form of a compacted tablet.

In one embodiment, the at least one active agent and/or inactive agent is/are in form of a core which is at least partially covered by the at least one hot melt extruded polymer resin comprising the at least one functionalized calcium carbonate-comprising material (FCC) and the at least one active agent and/or inactive agent is/are loaded onto or mixed with the at least one functionalized calcium carbonate-comprising material (FCC). It is appreciated that the at least one active agent and/or inactive agent loaded onto or mixed with the at least one functionalized calcium carbonate-comprising material (FCC) and being in form of a core may be the same or different.

If present, the at least one excipient is present in the core, preferably a compacted tablet, which is at least partially covered by the at least one hot melt extruded polymer resin comprising the at least one functionalized calcium carbonate-comprising material (FCC). In one embodiment, also the layer at least partially covering the core comprises at least one excipient. It is appreciated that the at least one excipient in the core and the layer at least partially covering the core may be the same or different.

According to one aspect of the present application a method for producing a dosage form is provided. The method is characterized by the steps of
   a) providing at least one functionalized calcium carbonate-comprising material (FCC), which is a reaction product of natural ground calcium carbonate or precipitated calcium carbonate with carbon dioxide and one or more $H_3O^+$ ion donors, wherein the carbon dioxide is formed in situ by the $H_3O^+$ ion donors treatment and/or is supplied from an external source, as defined herein;
   b) providing at least one polymer resin;
   c) mixing the at least one functionalized calcium carbonate-comprising material of step a) and the at least one polymer resin of step b);
   d) hot melt extruding the mixture obtained in step c); and
   e) milling or pelletizing the hot melt extruded product obtained in step d) for obtaining the dosage form.

With regard to the definition of the at least one functionalized calcium carbonate-comprising material, the at least one polymer resin and preferred embodiments thereof, reference is made to the statements provided above when discussing the technical details of the dosage form of the present invention.

As regards the at least one polymer resin, it is to be noted that the material provided in step b) corresponds to the polymer resin before being hot melt extruded and thus forming the hot melt extruded polymer resin.

In one embodiment, the method further comprises a step b1) of providing at least one active agent and/or inactive agent and/or a step b2) of providing at least one excipient.

With regard to the definition of the active agent and/or inactive agent, at least one excipient and preferred embodiments thereof, reference is made to the statements provided above when discussing the technical details of the dosage form of the present invention.

If the dosage form comprises at least one active agent and/or inactive agent and/or at least one excipient which is/are loaded onto or mixed with the at least one functionalized calcium carbonate-comprising material (FCC), it is appreciated that the method further comprises a step of loading or mixing the at least one active agent and/or inactive agent and/or at least one excipient onto the at least one functionalized calcium carbonate-comprising material (FCC) prior to mixing step c). Such loading or mixing can be achieved by any conventional method known to the skilled person. For example, the step of loading onto or mixing the at least one active agent and/or inactive agent and/or at least one excipient with the at least one functionalized calcium carbonate-comprising material (FCC) takes place under mixing conditions. The skilled man will adapt these mixing conditions and configurations of mixing devices, such as mixer and/or blender, preferably a mixer such as a tumbling mixer, or any other devices suitable for this operation, according to his needs. However, the listed devices are not to be considered to be of limiting character.

According to step c) of the present method, the at least one functionalized calcium carbonate-comprising material of step a) and the at least one polymer resin of step b) are mixed.

If the dosage form comprises at least one active agent and/or inactive agent and/or at least one excipient which is/are dispersed in the at least one hot melt extruded polymer resin comprising the at least one functionalized calcium carbonate-comprising material (FCC), it is appreciated that the at least one active agent and/or inactive agent of step b1) and/or the at least one excipient of step b2) is/are preferably mixed with the at least one functionalized calcium carbonate-comprising material of step a) and the at least one polymer resin of step b) in mixing step c) prior to hot melt extruding step d).

Mixing the at least one functionalized calcium carbonate-comprising material of step a), the at least one polymer resin of step b) and the optionally at least one active agent and/or inactive agent of step b1) and/or the at least one excipient of step b2) can be carried out simultaneously or separately in any order to form a mixture.

The components provided in step a), step b), and optionally step b1) and/or step b2) can be mixed by any conventional means known to the skilled person. However, mixing step c) preferably takes place in a mixer and/or blender, preferably a mixer such as a tumbling mixer.

In one embodiment of the present invention, method step c) is carried out in that the at least one functionalized calcium carbonate-comprising material of step a) and the at least one active agent and/or inactive agent of step b1) and/or the at least one excipient of step b2) is combined simultaneously with the at least one polymer resin of step b). For example, method step c) is carried out in that the at least one polymer resin of step b) is combined with a blend of the at least one functionalized calcium carbonate-comprising material of step a) and the at least one active agent and/or inactive agent of step b1) and/or the at least one excipient of step b2). That is to say, said at least one functionalized calcium carbonate-comprising material of step a) and the at least one active agent and/or inactive agent of step b1) and/or the at least one excipient of step b2) may be pre-mixed prior to addition to said at least one polymer resin of step b).

Preferably, mixing step c) is carried out in that the at least one functionalized calcium carbonate-comprising material of step a) and the at least one active agent and/or inactive agent of step b1) and/or the at least one excipient of step b2) are added independently from each other to the at least one polymer resin of step b). According to step d) of the present method, the mixture obtained in step c) is hot melt extruded.

Hot melt extrusion is carried out with any conventional hot melt extruder known to the skilled person. For example, hot melt extrusion is carried out with a twin screw hot melt extruder with perforated die (e.g. Three-Tec, ZE9 20602, Switzerland). The skilled man will adapt the extrusion conditions and configurations of the hot melt extruder according to his needs.

According to step e) of the present method, the hot melt extruded product obtained in step d) is milled or pelletized for obtaining the dosage form. Such milling or pelletizing can be carried out with any conventional milling or pelletizing means known to the skilled person. For example, milling is carried out with a IKA A11 of IKA, Germany.

The term "milling" in the meaning of the present invention refers to a process of decreasing the size of the dosage form obtained in step d), preferably the dosage form obtained should be free flowing and provide no or only little dusting properties. For example, the dosage form has a Hausner ratio in the range from 1.0 to 1.34. The term "pelletizing" in the meaning of the present invention refers to a process of compacting or moulding the dosage form obtained in step d) into the shape of a pellet or granule.

For example, the hot melt extruded product obtained in step d) is cryo-milled for obtaining the dosage form. In this embodiment, the hot melt extruded product obtained in step d) is frozen, e.g. by using liquid nitrogen, and then milled.

In one embodiment of the present method, the method comprises one or more steps f) of compacting the dosage form obtained in step e). In compacting step f), tablets or granules are preferably obtained.

Additionally or alternatively, the hot melt extruded product obtained in step d) can be subjected to a compaction step d1) before milling or pelletizing step e) is carried out.

It is preferred that optional method step f) and/or step d1) is/are carried out at a compressive force in the range from 5 to 500 kN. It is to be noted that the compressive force used in step f) and/or step d1) depend(s) on the specific at least one functionalized calcium carbonate-comprising material provided in step a) and the at least one polymer resin provided in step b). The skilled person will thus adapt the compressive force accordingly. Preferably, optional compacting step f) and/or step d1) is/are carried out at a compressive force in the range from 6 to 300 kN, and most preferably in the range from 8 to 200 kN. For example, optional compacting step f) and/or step d1) is/are carried out at a compressive force in the range from 8 to 100 kN, and most preferably in the range from 8 to 50 kN or from 8 to 28 kN.

It is appreciated that the dosage form obtained in step e) may be sieved after step e), and, if present before step f). Such sieving can be carried out with any conventional sieving means known to the skilled person. The sieving can be carried out using one or more mesh sizes. Suitable mesh sizes are, but not limited to mesh sizes in the order of 180 μm, 250 μm, 355 μm, 500 μm and 710 μm.

If the dosage form comprises at least one active agent and/or inactive agent and/or at least one excipient which is/are in form of a layer which at least partially covers a core, preferably a compacted tablet, made from the at least one hot melt extruded polymer resin comprising the at least one functionalized calcium carbonate-comprising material (FCC), it is appreciated that the at least one active agent and/or inactive agent of step b1) and/or the at least one excipient of step b2) is/are preferably coated in form of one or more layers onto the dosage form obtained in step e).

According to one embodiment of the present invention, the method comprising the steps a) to e) and further comprising the steps b1) and/or b2) as mentioned above, comprises the step c) of mixing the at least one functionalized calcium carbonate-comprising material of step a), the at least one polymer resin of step b) and the at least one active agent and/or inactive agent of step b1) and/or at least one excipient of step b2), and optionally further comprises step f) of compacting the dosage form obtained in step e).

For example, the method comprising the steps a) to e) and further comprising the steps b1) and b2) as mentioned above, comprises the step c) of mixing the at least one functionalized calcium carbonate-comprising material of step a), the at least one polymer resin of step b) and the at least one active agent and/or inactive agent of step b1) and at least one excipient of step b2), and optionally further comprises step f) of compacting the dosage form obtained in step e).

If the dosage form further comprises, the same or different, at least one active agent and/or inactive agent and/or at least one excipient which is/are loaded onto or mixed with the at least one functionalized calcium carbonate-comprising material (FCC), the method comprising the steps a) to e) and further comprising the steps b1) and/or b2) as mentioned above, comprises loading onto or mixing the at least one active agent and/or inactive agent of step b1) and/or at least one excipient of step b2) with the at least one functionalized calcium carbonate-comprising material (FCC) prior to mixing step c), the step c) of mixing the at least one functionalized calcium carbonate-comprising material of step a), i.e. the loaded functionalized calcium carbonate-comprising material (FCC), the at least one polymer resin of step b) and the same or different at least one active agent and/or inactive agent of step b1) and/or at least one excipient of step b2), and optionally further comprises step f) of compacting the dosage form obtained in step e).

For example, the method comprising the steps a) to e) and further comprising the steps b1) and b2) as mentioned above, comprises loading onto or mixing the at least one active agent and/or inactive agent of step b1) with the at least one functionalized calcium carbonate-comprising material (FCC) prior to mixing step c), the step c) of mixing the at least one functionalized calcium carbonate-comprising material of step a), i.e. the loaded functionalized calcium carbonate-comprising material (FCC), the at least one polymer resin of step b) and the same or different at least one active agent and/or inactive agent of step b1) and at least one excipient of step b2), and optionally further comprises step f) of compacting the dosage form obtained in step e).

According to another embodiment of the present invention, the method comprising the steps a) to e) and further comprising the steps b1) and/or b2) as mentioned above, comprises the step c) of mixing the at least one functionalized calcium carbonate-comprising material of step a), the at least one polymer resin of step b) and the at least one active agent and/or inactive agent of step b1) and/or the at least one excipient of step b2), coating the at least one active agent and/or inactive agent of step b1) and/or the at least one excipient of step b2) in form of one or more layers onto the dosage form obtained in step e) and optionally further comprises step f) of compacting the dosage form obtained after coating.

For example, the method comprising the steps a) to e) and further comprising the steps b1) and b2) as mentioned above, comprises the step c) of mixing the at least one functionalized calcium carbonate-comprising material of step a), the at least one polymer resin of step b) and the at least one excipient of step b2), coating the at least one active agent and/or inactive agent of step b1) and the same or different at least one excipient of step b2) in form of one or more layers onto the dosage form obtained in step e) and optionally further comprises step f) of compacting the dosage form obtained after coating.

If the dosage form further comprises, the same or different, at least one active agent and/or inactive agent and/or at least one excipient which is/are loaded onto or mixed with the at least one functionalized calcium carbonate-comprising material (FCC), the method comprising the steps a) to e) and further comprising the steps b1) and/or b2) as mentioned above, comprises loading onto or mixing the at least one active agent and/or inactive agent of step b1) and/or at least one excipient of step b2) with the at least one functionalized calcium carbonate-comprising material (FCC) prior to mixing step c), the step c) of mixing the at least one functionalized calcium carbonate-comprising material of step a), i.e. the loaded functionalized calcium carbonate-comprising material (FCC), the at least one polymer resin of step b) and the same or different at least one active agent and/or inactive agent of step b1) and/or the at least one excipient of step b2), coating the same or different at least one active agent and/or inactive agent of step b1) and/or the at least one excipient of step b2) in form of one or more layers onto the dosage form obtained in step e) and optionally further comprises step f) of compacting the dosage form obtained after coating.

For example, the method comprising the steps a) to e) and further comprising the steps b1) and b2) as mentioned above, comprises loading onto or mixing the at least one active agent and/or inactive agent of step b1) with the at least one functionalized calcium carbonate-comprising material (FCC) prior to mixing step c), the step c) of mixing the at least one functionalized calcium carbonate-comprising material of step a), i.e. the loaded functionalized calcium carbonate-comprising material (FCC), the at least one polymer resin of step b) and the at least one excipient of step b2), coating the same or different at least one active agent and/or inactive agent of step b1) and/or the at least one excipient of step b2) in form of one or more layers onto the dosage form obtained in step e) and optionally further comprises step f) of compacting the dosage form obtained after coating.

If the dosage form is in form of a layered structure of at least two layers, wherein at least one layer is made from the hot melt extruded polymer resin comprising the at least one functionalized calcium carbonate-comprising material (FCC), the method comprising the steps a) to e) and further comprising the steps b1) and/or b2) as mentioned above, comprises the step c) of mixing the at least one functionalized calcium carbonate-comprising material of step a), the at least one polymer resin of step b) and the at least one active agent and/or inactive agent of step b1) and/or the at least one excipient of step b2) and further comprises step f) of compacting the dosage form obtained in step e) into a layered structure.

In an alternative embodiment, a tablet-in-cup is prepared. In this case, the at least one active agent and/or inactive agent of step b1) and/or the at least one excipient of step b2) is/are preferably mixed and compacted in compacting step f1) to form a core tablet.

The at least one active agent and/or inactive agent of step b1) and/or the at least one excipient of step b2) can be mixed by any conventional means known to the skilled person. However, the mixing of the at least one active agent and/or inactive agent of step b1) and/or the at least one excipient of step b2) preferably takes place in a mixer and/or blender, preferably a mixer such as a tumbling mixer.

In one embodiment, the at least one active agent and/or inactive agent of step b1) and/or the at least one excipient of step b2) is/are sieved prior mixing. Such sieving can be carried out with any conventional sieving means known to the skilled person. The sieving can be carried out using one or more mesh sizes. Suitable mesh sizes are, but not limited to mesh sizes in the order of 180 μm, 250 μm, 355 μm, 500 μm and 710 μm, e.g. 500 μm.

Compacting method step f1) is carried out at a compressive force in the range from 5 to 500 kN It is to be noted that the compressive force used in step f1) depends on the specific at least one active agent and/or inactive agent of step b1) and/or the at least one excipient of step b2). The skilled person will thus adapt the compressive force accordingly. Preferably, compacting step f1) is carried out at a compressive force in the range from 6 to 300 kN, and most preferably in the range from 8 to 200 kN. For example, compacting step f1) is carried out at a compressive force in the range from 8 to 100 kN, and most preferably in the range from 8 to 50 kN or from 8 to 28 kN.

Furthermore, the method further comprises a step g) of at least partially covering the core tablet formed in step f1) with the dosage form obtained in step e) and compacting the obtained product.

The compacting is preferably carried out at a compressive force in the range from 5 to 500 kN. It is to be noted that the compressive force used in step f1) depends on the specific at least one active agent and/or inactive agent of step b1) and/or the at least one excipient of step b2) and the hot melt extruded polymer resin comprising the at least one functionalized calcium carbonate-comprising material (FCC). The skilled person will thus adapt the compressive force accordingly. Preferably, the compacting f1) is carried out at a compressive force in the range from 6 to 300 kN, and most preferably in the range from 8 to 200 kN. For example, the compacting is carried out at a compressive force in the range from 8 to 100 kN, and most preferably in the range from 8 to 50 kN or from 8 to 28 kN.

It is appreciated that this method, i.e. the preparation of a tablet-in-cup, can comprise a further step of loading the same or different at least one active agent and/or inactive agent of step b1) and/or at least one excipient of step b2) is/are onto the at least one functionalized calcium carbonate-comprising material (FCC) prior to mixing step c).

Additionally or alternatively, this method, i.e. the preparation of a tablet-in-cup, can comprise a further step of mixing the same or different at least one active agent and/or inactive agent of step b1) and/or at least one excipient of step b2) with the at least one functionalized calcium carbonate-comprising material of step a) and the at least one polymer resin of step b) in mixing step c) prior to hot melt extruding step d).

The inventors surprisingly found out that present method for producing a dosage form results in a dosage form that is lighter and less voluminous at higher drug load, especially compared to a conventional dosage form comprising a functionalized calcium carbonate-comprising material. Further the dosage form can be prepared in a highly efficient compression method without the use of binders and/or compacting aids.

In view of the good results obtained, the present application refers in another aspect to the use of a functionalized calcium carbonate-comprising material (FCC) in a method for producing a dosage form. According to another aspect, the use of a functionalized calcium carbonate-comprising material (FCC) in a dosage form such as a tablet, mini-tablet, pellet, capsule, granule and/or a tablet-in-cup is provided.

With regard to the definition of the at least one functionalized calcium carbonate-comprising material and preferred embodiments thereof, reference is made to the statements provided above when discussing the technical details of the dosage form of the present invention.

EXAMPLES

1. Materials

Figure 1:
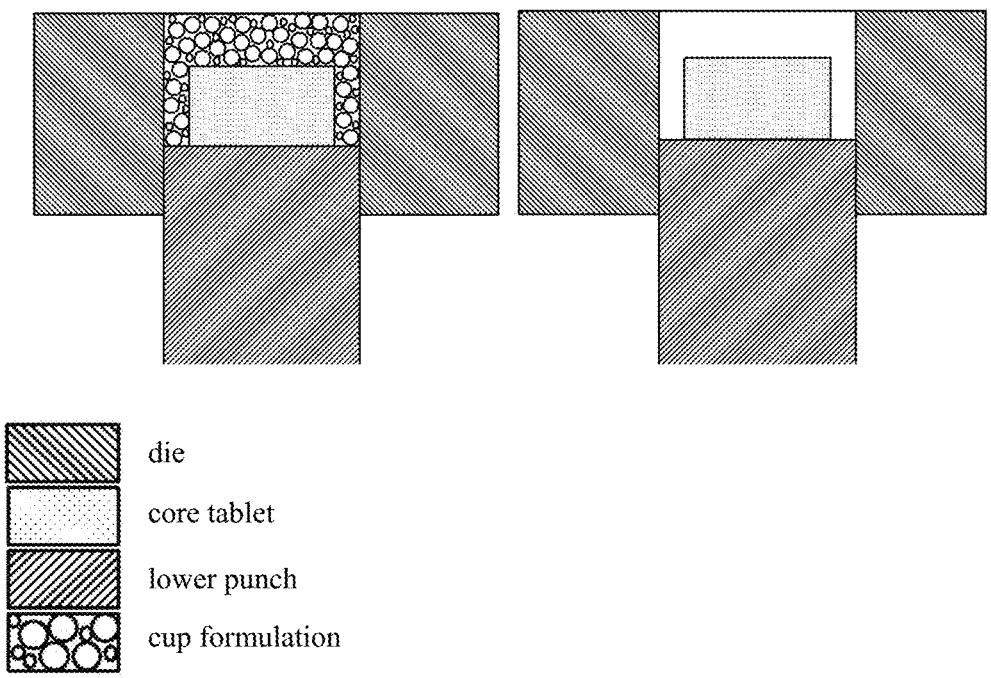
FIG. 1 refers to the schematic representation of the TIC compaction.

The core tablet consisted of 96% (m/m) metformin HCl (Harman Finochem Limited), 2% (m/m) polyvinylalcohol (PVA) and 2% (m/m) Carbopol 980 NF (Lubrizol, Advanced Materials, Belgium).

Formulation for the cup consists of a 1:1 (m/m) mix of functionalized calcium carbonate (FCC) (Omya International AG, Switzerland, BET specific surface area of 62.8 m$^2$/g, $d_{50}$ of 11.7 μm, $d_{98}$ of 26.7 μm) and polycaprolacton (Capa 6506, Perstorp UK Limited). Magnesium stearate (Sandoz, Switzerland) was used for lubrication.

Kombiglyze® XR 5 mg/500 mg (Astra Zeneca, US) was taken as a reference.

2. Methods

Scanning Electron Microscopy (SEM)

Scanning electron microscopy (SEM) pictures were made with FEI Nova Nano SEM 230. The samples were sputtered with a 20-40 nm gold layer by a LEICA EM ACE600 Double Sputter coater.

Preparation of the Core Tablet

All excipients were sieved (<500 μm) and blended using the Turbula blender (T2C, W. A. Bachofer, Switzerland) with the speed 32 rpm for 10 min. This core formulation was compacted on Styl'One compaction simulator (Medel'pharm, France) with a 10 mm flat punch. Compaction cycle was defined with the following speed sections: Filling 2 sec, upper punch approach 1.5 sec, compaction 70 msec, relaxation 1.0 sec, ejection 5 sec and tablet selection 70 msec. Compaction force was set at 17 kN.

Preparation of the Cup Formulation

For the cup formulation hot melt granulation was carried out on a twin screw hot-melt extruder with perforated die (Three-Tec, ZE9 20602, Switzerland). The 5 heat cells were adjusted to following temperatures: Cell 1: 10° C., cell 2: 50° C. and cell 3, 4, 5 to 80° C. Feed rate was set between 3.1 g/in and 4.5 g/min. Twin screws were set at 100 rpm. The extruded product was cryo-milled with an IKA A11 (IKA, Germany) single-speed hand-mill with cut-tooling. The milled product was sieved through a 500 μm sieve. To analyze the cup formulation, a deformation profile was performed with 11.28 mm flat Euro D punch using compaction pressures from 50 MPa to 300 MPa.

Preparation of the Tablet-in-Cup (TIC)

The compaction of the TIC was carried out with a 13 mm beveled punch. Cycle was defined with following speed sections: Filling 2 sec, upper punch approach 10 sec, compaction 70 msec, relaxation 0.14 sec, ejection 70 msec and tablet selection 70 msec. Compaction force was set at 20 kN. Filling height was set at 9.2 mm, the core was placed centered on the lower punch and cup formulation (<500 μm) was filled in the die manually; see FIG. 1.

Hardness Test

The empty cups for hardness testing were produced the same way as the TIC-device but instead of a core tablet, a metal tablet was used as a template. After compaction the metal tablet was removed. Hardness testing (TIC n=6; core n=6, cup without core n=3) was carried out with Dr. Schleuniger Tablet Tester 8M (Switzerland).

Compressability, Compactability, Dissolution and Friability

Compressibility of the FCC-PCL composite was investigated using the Heckel equation (eq. 1) [R. Heckel, "Density-pressure relationships in powder compaction," *Trans. Metall. Soc. AIME*, vol. 221, pp. 671-675, 1961]:

$$\ln\left(\frac{1}{1-\rho}\right) = k \cdot \sigma + A, \tag{eq.1}$$

Where k is the Heckel parameter (MPa$^{-1}$), σ is the compressive pressure (MPa), ρ is the density of the tablet (g/cm³) and A is a constant. Compressive stress was varied between 45 MPa and 295 MPa. Density of the tablet was calculated according to equation 2 [J. Ilkka and P. Paronen, "Prediction of the compression behaviour of powder mixtures by the Heckel equation," *Int. J. Pharm.*, vol. 94, no. 1-3, pp. 181-187, June 1993]:

$$\rho = \frac{\left(\frac{m}{\pi \cdot r^2 h}\right)}{\rho_{true}}, \tag{eq.2}$$

Where m is the mass of the tablet (g), r is the radius of the tablet (cm), h is the tablet height and $\rho_{true}$ is the true density of the material (g/cm³). The yield pressure was calculated by taking the reciprocal of the Heckel slope (eq. 3) [J. Ilkka and P. Paronen, "Prediction of the compression behaviour of powder mixtures by the Heckel equation," *Int. J. Pharm.*, vol. 94, no. 1-3, pp. 181-187, June 1993]

$$\left(\sigma_y = \frac{1}{k}\right) \tag{eq.3}$$

In order to investigate compaction susceptibility of the material, modified Heckel equation (eq. 4) was used [M. Kuentz and H. Leuenberger, "Pressure susceptibility of polymer tablets as a critical property: A modified heckel equation," *J. Pharm. Sci.*, vol. 88, no. 2, pp. 174-179, February 1999]:

$$\sigma = \frac{1}{C}\left[\rho_{ro} - \rho - (1-\rho_{ro}) \cdot \ln\left(\frac{1-\rho}{1-\rho_{ro}}\right)\right], \tag{eq.4}$$

Where σ is the compressive pressure (MPa), C is a constant (MPa⁻¹), $\rho_{rc}$ is the critical density (g/cm³) and ρ is the relative tablet density (g/cm³).

Powder compactibility was investigated by plotting tensile strength as a function of compressive pressures [H. Leuenberger and B. D. Rohera, "Fundamentals of Powder Compression. I. The Compactibility and Compressibility of Pharmaceutical Powders," *Pharm. Res.*, vol. 3, no. 1, pp. 12-22, February 1986]. Tensile strengths were calculated according to equation 5 for round tablets and according to equation 6 for shaped tablets ["The United States Pharmacopoeia.," [Online]. Available: http://www.drugfuture.com/pharmacopoeia/usp32/pub/data/v32270/usp32nf27s0_c1217.html]:

$$\sigma_t = \frac{2 \cdot F}{\pi \cdot d \cdot h}, \tag{eq.5}$$

$$\sigma_t = \frac{10 \cdot F}{\pi D^2 \cdot \left(2.04\frac{t}{D} - 0.126\frac{t}{W} + 3.15\frac{W}{D} + 0.01\right)}, \tag{eq.6}$$

Where $\sigma_t$ is the tensile strength (MPa), F is the crushing force (N), d is the diameter (mm) of the round tablets and h the height of the round tablet (mm). For shaped tablet D is the tablet width, t is the tablet height and W is the shaft height (mm). Information about the deformation of the material under stress and the bonding properties of the material was assessed by calculating the factors compactibility and compression susceptibility using Leuenberger equation 7 [H. Leuenberger and B. D. Rohera, "Fundamentals of Powder Compression. I. The Compactibility and Compressibility of Pharmaceutical Powders," *Pharm. Res.*, vol. 3, no. 1, pp. 12-22, February 1986]:

$$\sigma_t = \sigma_{t\,max} \cdot (1 - e^{(-\gamma \cdot \sigma \cdot \rho)}). \tag{eq.7}$$

Where $\sigma_t$ is the tensile strength, $\sigma_{t\,max}$ is the tensile strength when compressive pressure (σ)→∞ and relative density (ρ)→1, γ is the compression susceptibility and σ is the applied compressive pressure. Data from 50 MPa to 300 MPa were included in the calculation.

Dissolution testing (TIC: n=6; Kombiglyze®XR: n=3, cores n=6) was carried out on SOTAX AT7 Smart (Sotax, Switzerland) connected to a UV-spectrometer (Amersham Biosciences, Ultraspec 3100pro, UK) with a Sotax CY 7-50 pump (Sotax, Switzerland). Dissolution profile was measured in water (37° C.), USP apparatus 2, 50 rpm over 24 hours for TIC and Kombiglyze®XR and 3 hours for the cores respectively. The spectrometer was set to 250 nm, concentration were calculated according the following equation 8:

$$y = 0.0015x + 0.0102, R^2 = 0.9998 \tag{eq.8}$$

Friability (n=10) was tested by using Erweka TA200 (Erweka, Germany).

F2 criterion was calculated according to the FDA [U.S. Department of Health and Human Services, Food and Drug Administration, and Center for Drug Evaluation and Research (CDER), "Guidance for Industry, Dissolution Testing of Immediate Release Solid Oral Dosage Forms." August-1997] as set out in equation 9:

$$f_2 = 50 \cdot \log\left\{\left[1 + \frac{1}{n}\Sigma(R_t - T_t)^2\right]^{-0.2} \cdot 100\right\}, \tag{eq.9}$$

where Rt is the drug release in % (m/m) at time t of the reference sample and Tt is the drug release in % (m/m) at time t of the test sample, n=146.

Tensile Strength

Tensile strength was calculated with equation 10:

$$\sigma_t = \frac{S \times F}{\pi \times d \times h} \tag{eq.10}$$

where $\sigma_t$ is the radial tensile strength (MPa), F is the crushing force (N), d is the tablet diameter (mm), and h is the tablet thickness (mm). Crushing forces were measured with a tablet hardness tester (8M, Dr. Schleuniger Pharmatron, Switzerland).

3. Results

To produce the cup formulation, e.g. a FCC-PCL composite, first FCC and PCL were mixed and then hot melt granulation was carried out. During hot melt granulation, torque remained constant at 3.21±0.04 Nm. Temperatures of cell 3, cell 4 and cell 5 were 80.12±0.66° C., 80.02±2.31° C. and 80.20±3.01° C., respectively. Only the temperatures of cell 3 to 5 were taken into consideration as polymer melting is happening in these cells only. The production of the FCC-PCL composite used to form the cup did not pose problems.

Figure 2:
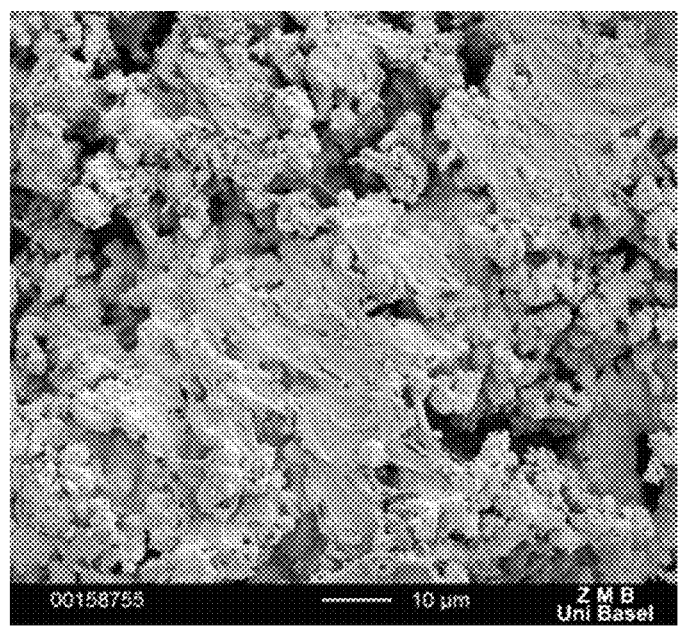
FIG. 2 refers to a scanning electron microscope picture of a granule.
Figure 3:
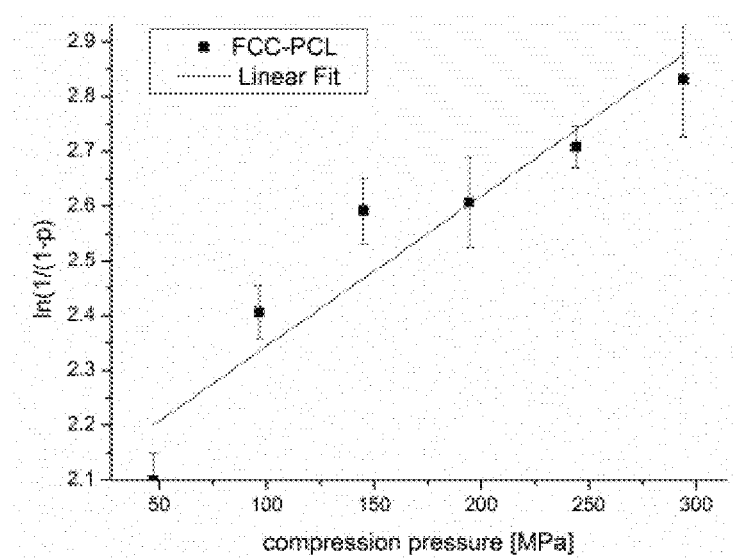
FIG. 3 refers to the Heckel plot of the FCC-PCL.
Figure 4:
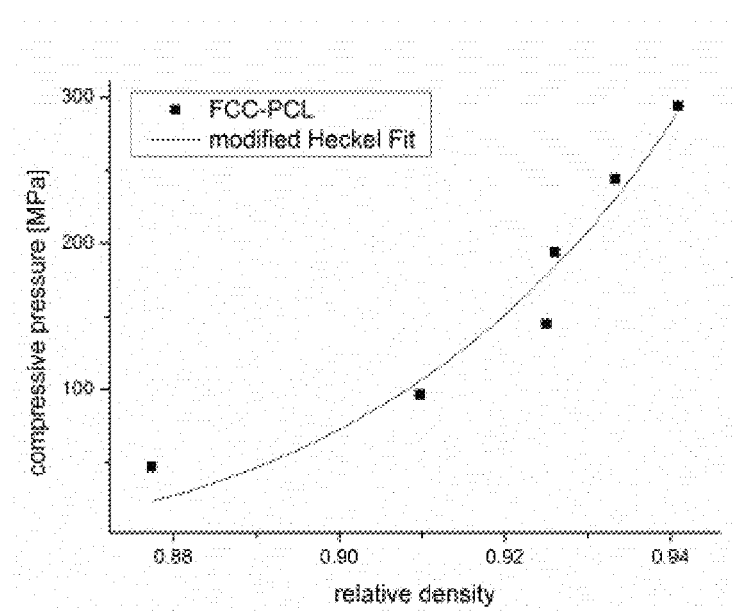
FIG. 4 refers to the modified Heckel plot of the FCC-PCL
FIG. 5 refers to the Leuenberger plot of the FCC-PCL.
Figure 5:
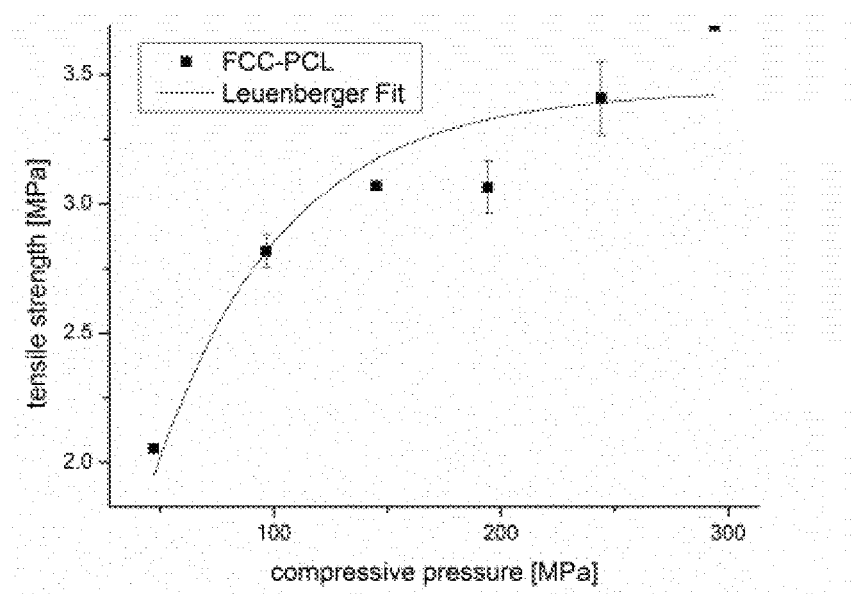

After granulation, the product was frozen, milled and sieved. FIG. 2 shows a SEM picture of the granules with the lamellar structure of FCC embedded in PCL. Only the granules with the size <500 μm were further used. The results of Heckel, modified Heckel and Leuenberger analysis are shown in Table 1. FIGS. 3, 4 and 5 show the Heckel plot, modified Heckel plot and Leuenberger plot.

TABLE 1

Results for the FCC-PCL composite

| Parameters | Values for FCC-PCL composite |
|---|---|
| Heckel analysis | |
| k ($10^{-3}$ MPa$^{-1}$) ± SD | 2.65 ± 0.22 |
| A ± SD | 2.09 ± 0.04 |
| $\sigma_y$ (MPa) | 377.36 |
| adj.R$^2$ | 0.873 |
| Modified Heckel analysis | |
| C ($10^{-3}$ MPa$^{-1}$) | 0.20 ± 0.14 |
| $\rho_{rc}$ ± SD | 0.847 ± 0.04 |
| adj. R$^2$ | 0.940 |
| Leuenberger analysis | |
| $\sigma_{max}$ (MPa) ± SD | 3.44 ± 0.07 |
| γ ($10^{-3}$ MPa$^{-1}$) | 19.43 ± 1.11 |
| adj.R$^2$ | 0.870 |

From Heckel analysis the value for $\sigma_y$ is 377.36 MPa. This value is comparable with the results in a previous study, where the FCC alone had a yield pressure of $\sigma_y$=294 MPa [T. Stirnimann, S. Atria, J. Schoelkopf, P. A. C. Gane, R. Alles, J. Huwyler, and M. Puchkov, "Compaction of functionalized calcium carbonate, a porous and crystalline microparticulate material with a lamellar surface," *Int. J. Pharm.*, vol. 466, no. 1-2, pp. 266-275, May 2014]. The values are higher than reported in other studies, where plastically deforming material showed a yield pressure of 40-135 MPa [S. Jain, "Mechanical properties of powders for compaction and tableting: an overview," *Pharm. Sci. Technol. Today*, vol. 2, no. 1, pp. 20-31, January 1999]. It is shown that FCC-PCL, at a relative density of ρ=0.843, forms a stable compact.

From Leuenberger analysis the value for $\sigma_{tmax}$ yielded 3.44 MPa, which shows plastic behavior of the material. For γ a value of 19.43 $10^{-3}$ MPa$^{-1}$ was found. This value is high compared to the FCC investigated in the previous study and is significantly greater than the value for MCC (7.56*$10^{-3}$ MPa$^{-1}$) [T. Stimimann, S. Atria, J. Schoelkopf, P. A. C. Gane, R. Alles, J. Huwyler, and M. Puchkov, "Compaction of functionalized calcium carbonate, a porous and crystalline microparticulate material with a lamellar surface," *Int. J. Pharm.*, vol. 466, no. 1-2, pp. 266-275, May 2014]. Such value indicates additional bonding action of PCL polymer on FCC lamellae. High values of γ indicate plastic behavior and that at already low compressive pressures the maximal tensile strength can be reached. Both values, γ and $\sigma_{tmax}$, show the good bonding properties of the material.

The core tablets and cup material were compacted to form the TIC device. The parameters of the core tablets, which were subsequently compacted to the TIC device, are shown in Table 2. Resulting parameters of the TIC device (i.e., core compacted in the cup), are also shown in Table 2 along with measured parameters of a reference product (Kombiglyze® XR). During hardness testing of the TIC, core and cup were not falling apart. Separately, the hardness of the cup was assessed without core tablet and yielded 90.50±4.68 N.

TABLE 2

Parameters of the core, TIC and reference

| Average | Core | TIC | Reference |
|---|---|---|---|
| Weight [mg] | 517.46 ± 2.32 | 994.53 ± 5.67 | 1197.90 ± 9.87 |
| Diameter [mm] | 10.03 ± 0.00 | 13.06 ± 0.00 | 9.78 ± 0.02* \| 19.60 ± 0.02# |
| Height [mm] | 5.36 ± 0.03 | 5.70 ± 0.03 | 7.20 ± 0.02 |
| Hardness [N] | 127.00 ± 8.63 | 261.33 ± 15.19 | 297.33 ± 45.83 |
| Tensile strength [MPa] | 1.50 ± 0.11 | 2.24 ± 0.12 | 3.33 ± 0.05 |
| Volume [mm$^3$] | 423.49 ± 2.16 | 755.05 ± 4.01 | 985.7 |
| Friability [%] | — | 0.00** | — |
| Drug load [%] | 96.63 | 50.27 | 41.73 |

Figure 6:
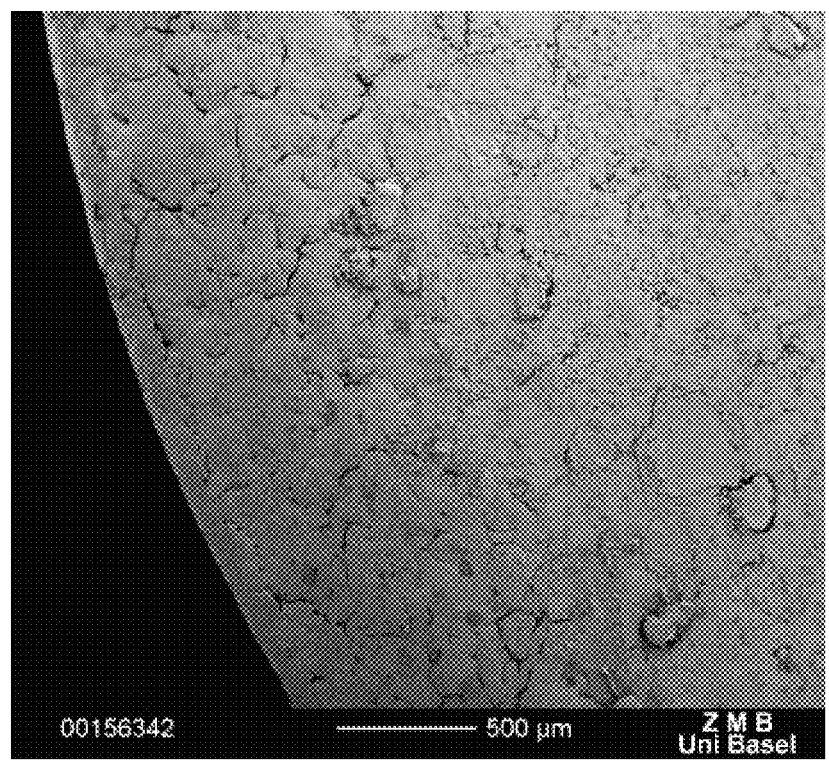
FIG. 6 refers to a scanning electron microscope picture of the tablet-in-cup (TIC).

*width of oblong tablet, #length of oblong tablet, no mass change was detected The flow of the cup material under compaction was excellent for both, slow (10 sec) and fast (70 msec) compaction cycles. In both cases the cup material distribution was homogeneous i.e. forming equally-sized cup walls, without cracks, ruptures or gaps. An example of a compacted cup is shown in FIG. 6**.

The release profiles of the reference (Kombiglyze®XR 5 mg/500 mg) and the TIC show that the release profile of the TIC is slightly slower than the profile of the reference. Showing a linear section between 200 min and 800 min. Standard deviation was not more than 1.33% (m/m) in the case of the reference and not more than 2.58% in the case of the TIC. The f2 test yielded a value of 78.60, hence the dissolution profiles can be considered as being identical.

The parameters of the tablets show that the TIC is 203 mg lighter than the reference. Hence, drug load is 8.5% higher in the TIC compared to the reference. The TIC device is less voluminous (754.27±3.82 mm$^3$) compared to the reference (985.7 mm$^3$), which makes it easier to swallow. The amount of excipient to control the release was 20 mg; this is 2% (m/m) of the total mass of the TIC.

During friability test no mass change was detected. The TIC devices are stable and showed no breakage or deformation, hence a coating is not required. The cup without core tablet was stable with a hardness of 90.50 N which is not surprising due to the values γ and $\sigma_{tmax}$ indicating good bonding at low compressive stresses. As shown in FIG. 6 the connection between core and cup is tight and hence no dose dumping can be expected. Friability was undetectable. This shows high stability of the cup and its ability to stabilize the core.

Furthermore, it is to be noted that the FCC-PCL composite material is suitable for human consumption and biodegradable.

The invention claimed is:

1. A carrier for a pharmaceutical, nutraceutical, cosmetic, home and personal care product dosage form consisting of a hot melt extruded composition of:
   a) at least one functionalized calcium carbonate-comprising material which is a reaction product of natural ground calcium carbonate or precipitated calcium carbonate with carbon dioxide and one or more $H_3O^+$ ion donors, wherein the carbon dioxide is formed in situ by the one or more $H_3O^+$ ion donors treatment and/or is supplied from an external source, and
   b) at least one polymer resin selected from the group comprising polyethylene, polystyrene, polyvinylchloride, polyamide 66 (nylon), polycaprolactame, polycaprolactone, acrylic polymers, acrylonitrile butadiene styrene, polybenzimidazole, polycarbonate, polyphenylene oxide/sulfide, polypopylene, teflon, polylactic acid, polylactic acid-based polymer, and aliphatic polyester, wherein the at least one functionalized calcium carbonate-comprising material is dispersed in the composition and the weight ratio of functionalized calcium carbonate-comprising material to polymer resin ranges from 95:5 to 5:95;

wherein the carrier is a powder, tablets, mini-tablets, granules, pellets, capsules or tablet-in-cup and c) an optional active ingredient, wherein the active agent is i) loaded onto or mixed with the composition, ii) dispersed in the composition, iii) is in form of a core, which is at least partially covered by the composition, or iv) in form of a layer which at least partially covers a core, made from the composition, or e) in form of a layered structure of at least two layers, wherein at least one layer is made from the composition.

2. The carrier of claim 1, wherein the natural ground calcium carbonate is selected from calcium carbonate containing minerals selected from the group comprising marble, chalk, dolomite, limestone and mixtures thereof, or the precipitated calcium carbonate is selected from the group comprising precipitated calcium carbonates having aragonitic, vateritic or calcitic mineralogical crystal forms and mixtures thereof.

3. The carrier according to claim 1, wherein the at least one functionalized calcium carbonate-comprising material:

a) has a BET specific surface area of from 20 $m^2/g$ to 450 $m^2/g$ measured using nitrogen and BET method according to ISO 9277; and/or b) comprises particles having a volume median grain diameter $d_{50}$ (vol) of from 1 μm to 50 μm; and/or has an intra-particle intruded specific pore volume within a range of 0.15 to 1.35 $cm^3/g$, calculated from a mercury intrusion porosimetry measurement.

4. A carrier for a pharmaceutical, nutraceutical, cosmetic, home and personal care product dosage form consisting of a hot melt extruded composition of:

a) at least one functionalized calcium carbonate-comprising material which is a reaction product of natural ground calcium carbonate or precipitated calcium carbonate with carbon dioxide and one or more $H_3O^+$ ion donors, wherein the carbon dioxide is formed in situ by the one or more $H_3O^+$ ion donors treatment and/or is supplied from an external source, b) at least one polymer resin selected from the group comprising polyethylene, polystyrene, polyvinylchloride, polyamide 66 (nylon), polycaprolactame, polycaprolactone, acrylic polymers, acrylonitrile butadiene styrene, polybenzimidazole, polycarbonate, polyphenylene oxide/sulfide, polypopylene, teflon, polylactic acid, polylactic acid-based polymer, and aliphatic polyester, and c) an active agent and/or a prodrug thereof;

wherein the at least one functionalized calcium carbonate-comprising material is dispersed in the composition and a weight ratio of functionalized calcium carbonate-comprising material to hot melt extruded polymer resin ranges from 95:5 to 5:95;

wherein the carrier is in form of powder, tablets, mini-tablets, granules, pellets, capsules or tablet-in-cup.

* * * * *

UNITED STATES PATENT AND TRADEMARK OFFICE
CERTIFICATE OF CORRECTION

Page 1 of 1

PATENT NO. : 11,737,984 B2
APPLICATION NO. : 16/304991
DATED : August 29, 2023
INVENTOR(S) : Wagner-Hattler et al.

It is certified that error appears in the above-identified patent and that said Letters Patent is hereby corrected as shown below:

In the Claims

In Column 48, Line 3, in Claim 3, before "has", insert --c)--

Signed and Sealed this
Seventh Day of October, 2025

John A. Squires
*Director of the United States Patent and Trademark Office*